(12) United States Patent
Miller et al.

(10) Patent No.: US 11,141,271 B2
(45) Date of Patent: *Oct. 12, 2021

(54) TISSUE ANCHOR FOR ANNULOPLASTY DEVICE

(71) Applicant: Valtech Cardio, Ltd., Or Yehuda (IL)

(72) Inventors: Eran Miller, Moshav Beit Elazari (IL); Oz Cabiri, Hod Hasharon (IL)

(73) Assignee: Valtech Cardio Ltd., Caesarea (IL)

(*) Notice: Subject to any disclaimer, the term of this patent is extended or adjusted under 35 U.S.C. 154(b) by 95 days.

This patent is subject to a terminal disclaimer.

(21) Appl. No.: 16/159,621

(22) Filed: Oct. 13, 2018

(65) Prior Publication Data
US 2019/0046318 A1    Feb. 14, 2019

Related U.S. Application Data

(63) Continuation of application No. 15/208,253, filed on Jul. 12, 2016, now Pat. No. 10,098,737, which is a (Continued)

(51) Int. Cl.
A61F 2/24 (2006.01)

(52) U.S. Cl.
CPC .... A61F 2/2445 (2013.01); *A61F 2220/0016* (2013.01)

(58) Field of Classification Search
CPC ...... A61B 17/0401; A61B 2017/00243; A61B 2017/0409; A61B 2017/0414;
(Continued)

(56) References Cited

U.S. PATENT DOCUMENTS

| 3,604,488 A | 9/1971 | Wishart et al. |
| 3,656,185 A | 4/1972 | Carpentier |

(Continued)

FOREIGN PATENT DOCUMENTS

| EP | 1034753 A1 | 9/2000 |
| EP | 3531975 A1 | 9/2019 |

(Continued)

OTHER PUBLICATIONS

Agarwal et al. International Cardiology Perspective Functional Tricuspid Regurgitation, Circ Cardiovasc Interv 2009;2;2;565-573 (2009).

(Continued)

*Primary Examiner* — Seema Mathew
(74) *Attorney, Agent, or Firm* — Thomas C. Richardson

(57) ABSTRACT

A tissue anchor is provided for use with a valve-repair implant configured to be coupled to cardiac tissue of a patient. The tissue anchor includes a distal tissue coupling element configured to couple the tissue anchor to the cardiac tissue of the patient. It further comprises a proximal implant-penetrating element configured to penetrate at least a portion of the valve-repair implant and facilitate coupling of the valve-repair implant to the tissue anchor. The proximal implant-penetrating element includes an implant-restraining element coupled to a portion of the implant-penetrating element. The implant-restraining element is configured to restrain the valve-repair implant from separating from the implant-penetrating element. Other applications of the present invention are also described.

18 Claims, 20 Drawing Sheets

Related U.S. Application Data continuation of application No. 14/667,090, filed on Mar. 24, 2015, now Pat. No. 9,414,921, which is a continuation of application No. 13/504,870, filed as application No. PCT/IL2010/000890 on Oct. 28, 2010, now Pat. No. 9,011,520, which is a continuation-in-part of application No. 12/608,316, filed on Oct. 29, 2009, now Pat. No. 8,277,502.

(58) Field of Classification Search
CPC .... A61B 2017/0441; A61B 2017/0464; A61B 2017/0496; A61B 2017/0649; A61B 2017/12095; A61F 2/2427; A61F 2/2457; A61F 2/2466; A61F 2/2487; A61F 2/24; A61F 2/2445; A61F 2/2448; A61F 2/2451; A61F 2/2442; A61F 2220/0016; A61F 2220/0025; A61F 2220/0033; A61F 2220/0041; A61F 2220/0091; A61F 2220/0083; A61F 2220/0008
See application file for complete search history.

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Ferrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,720,753 A * | 2/1998 | Sander ............... A61B 17/8872 606/104 |
| 5,728,116 A | 3/1998 | Rosenman |
| 5,730,150 A | 3/1998 | Peppel et al. |
| 5,749,371 A | 5/1998 | Zadini et al. |
| 5,782,844 A | 7/1998 | Yoon et al. |
| 5,810,882 A * | 9/1998 | Bolduc ............... A61B 17/064 606/151 |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpenter et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |

(56) References Cited

U.S. PATENT DOCUMENTS

| | | |
|---|---|---|
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz et al. |
| 6,964,686 B2 | 11/2005 | Gordon |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,087,064 B1 | 6/2006 | Hyde |
| 7,077,850 B2 | 7/2006 | Kortenbach |
| 7,077,862 B2 | 7/2006 | Vidlund et al. |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,780,726 B2 | 6/2010 | Seguin |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 | 7/2011 | Webler et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |

(56) References Cited

U.S. PATENT DOCUMENTS

| | | |
|---|---|---|
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Saiahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Aikhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,788,948 B2* | 10/2017 | Gilmore ............... A61N 1/0573 |
| 9,801,720 B2 | 10/2017 | Gilmore et al. |
| 9,883,857 B2* | 2/2018 | Shluzas ............... A61B 17/0057 |
| 9,907,547 B2 | 3/2018 | Gilmore et al. |
| 9,918,840 B2* | 3/2018 | Reich ................... A61F 2/2445 |
| 10,299,793 B2* | 5/2019 | Zipory ................. A61B 17/105 |
| 10,368,852 B2 | 8/2019 | Gerhardt et al. |
| 10,485,909 B2* | 11/2019 | Cotter ................. A61M 60/148 |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1* | 7/2002 | Brock ................... A61B 90/36 |
| | | 600/114 |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0018358 A1* | 1/2003 | Saadat ................. A61F 2/2445 |
| | | 606/232 |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |

(56) References Cited

U.S. PATENT DOCUMENTS

| | | |
|---|---|---|
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |
| 2003/0229395 A1 | 12/2003 | Cox |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Gear et al. |
| 2004/0044350 A1 | 3/2004 | Martin et al. |
| 2004/0059413 A1 | 3/2004 | Argento |
| 2004/0068273 A1 | 4/2004 | Fariss et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0236419 A1* | 11/2004 | Milo ............... A61B 17/0401 623/2.36 |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Randert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Vouohlohn |
| 2005/0049692 A1 | 3/2005 | Numarnoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0171601 A1 | 8/2005 | Cosgrove et al. |
| 2005/0177180 A1* | 8/2005 | Kaganov ............ A61B 17/068 606/151 |
| 2005/0177228 A1 | 8/2005 | Solem et al. |
| 2005/0187568 A1 | 8/2005 | Klenk et al. |
| 2005/0187613 A1* | 8/2005 | Bolduc ................ A61F 2/07 623/1.23 |
| 2005/0192596 A1 | 9/2005 | Jugenheirner et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0184242 A1 | 6/2006 | Lichtenstein |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276671 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0118151 A1* | 5/2007 | Davidson ........... A61B 17/0469 606/144 |
| 2007/0118154 A1 | 5/2007 | Crabtree |
| 2007/0118213 A1* | 5/2007 | Loulmet ............ A61B 17/0401 623/2.1 |
| 2007/0118215 A1 | 5/2007 | Moaddeb |
| 2007/0142907 A1 | 6/2007 | Moaddeb |
| 2007/0162111 A1 | 7/2007 | Fukamachi et al. |
| 2007/0198082 A1 | 8/2007 | Kapadia et al. |
| 2007/0219558 A1* | 9/2007 | Deutsch ............ A61B 17/0401 606/326 |
| 2007/0239208 A1 | 10/2007 | Crawford |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |

(56) References Cited

U.S. PATENT DOCUMENTS

| | | | |
|---|---|---|---|
| 2007/0282375 A1* | 12/2007 | Hindrichs | A61B 17/00234 606/232 |
| 2007/0282429 A1 | 12/2007 | Hauser et al. | |
| 2007/0295172 A1 | 12/2007 | Swartz | |
| 2007/0299424 A1 | 12/2007 | Cumming et al. | |
| 2008/0004697 A1 | 1/2008 | Lichtenstein et al. | |
| 2008/0027483 A1 | 1/2008 | Cartledge et al. | |
| 2008/0027555 A1 | 1/2008 | Hawkins | |
| 2008/0035160 A1 | 2/2008 | Woodson et al. | |
| 2008/0039935 A1 | 2/2008 | Buch et al. | |
| 2008/0051703 A1 | 2/2008 | Thornton et al. | |
| 2008/0058595 A1 | 3/2008 | Snoke et al. | |
| 2008/0065011 A1 | 3/2008 | Marchand et al. | |
| 2008/0065204 A1 | 3/2008 | Macoviak et al. | |
| 2008/0071366 A1 | 3/2008 | Tuval et al. | |
| 2008/0086138 A1* | 4/2008 | Stone | A61B 17/0401 606/265 |
| 2008/0086203 A1 | 4/2008 | Roberts | |
| 2008/0091169 A1 | 4/2008 | Heideman et al. | |
| 2008/0091257 A1 | 4/2008 | Andreas et al. | |
| 2008/0097483 A1 | 4/2008 | Ortiz et al. | |
| 2008/0097523 A1 | 4/2008 | Bolduc et al. | |
| 2008/0103572 A1 | 5/2008 | Gerber | |
| 2008/0140116 A1 | 6/2008 | Bonutti | |
| 2008/0167713 A1 | 7/2008 | Bolling | |
| 2008/0167714 A1 | 7/2008 | St. Goar et al. | |
| 2008/0177380 A1 | 7/2008 | Starksen et al. | |
| 2008/0195126 A1 | 8/2008 | Solem | |
| 2008/0195200 A1 | 8/2008 | Vidlund et al. | |
| 2008/0208265 A1 | 8/2008 | Frazier et al. | |
| 2008/0221672 A1 | 9/2008 | Lamphere et al. | |
| 2008/0234729 A1 | 9/2008 | Page et al. | |
| 2008/0262480 A1 | 10/2008 | Stahler et al. | |
| 2008/0262609 A1 | 10/2008 | Gross et al. | |
| 2008/0275300 A1 | 11/2008 | Rothe et al. | |
| 2008/0275469 A1 | 11/2008 | Fanton et al. | |
| 2008/0275551 A1 | 11/2008 | Alfieri | |
| 2008/0281353 A1 | 11/2008 | Aranyi et al. | |
| 2008/0281411 A1 | 11/2008 | Berreklouw | |
| 2008/0287862 A1 | 11/2008 | Weitzner et al. | |
| 2008/0288044 A1 | 11/2008 | Osborne | |
| 2008/0288062 A1 | 11/2008 | Andrieu et al. | |
| 2008/0300537 A1 | 12/2008 | Bowman | |
| 2008/0300629 A1 | 12/2008 | Surti | |
| 2008/0312506 A1 | 12/2008 | Spivey et al. | |
| 2009/0024110 A1 | 1/2009 | Heideman et al. | |
| 2009/0028670 A1 | 1/2009 | Garcia et al. | |
| 2009/0043381 A1 | 2/2009 | Macoviak et al. | |
| 2009/0054723 A1 | 2/2009 | Khairkhahan et al. | |
| 2009/0054969 A1 | 2/2009 | Salahieh et al. | |
| 2009/0062866 A1 | 3/2009 | Jackson | |
| 2009/0076586 A1 | 3/2009 | Hauser et al. | |
| 2009/0076600 A1 | 3/2009 | Quinn | |
| 2009/0088837 A1 | 4/2009 | Gillinov et al. | |
| 2009/0093877 A1 | 4/2009 | Keidar et al. | |
| 2009/0099650 A1 | 4/2009 | Bolduc et al. | |
| 2009/0105816 A1* | 4/2009 | Olsen | A61B 17/00234 623/2.37 |
| 2009/0125102 A1 | 5/2009 | Cartledge et al. | |
| 2009/0166913 A1 | 7/2009 | Guo et al. | |
| 2009/0171439 A1 | 7/2009 | Nissl | |
| 2009/0177266 A1 | 7/2009 | Powell et al. | |
| 2009/0177274 A1 | 7/2009 | Scorsin et al. | |
| 2009/0177277 A1* | 7/2009 | Milo | A61B 17/0644 623/2.36 |
| 2009/0248148 A1 | 10/2009 | Shaolian et al. | |
| 2009/0254103 A1 | 10/2009 | Deutsch | |
| 2009/0264994 A1 | 10/2009 | Saadat | |
| 2009/0287231 A1 | 11/2009 | Brooks et al. | |
| 2009/0287304 A1 | 11/2009 | Dahlgren et al. | |
| 2009/0299409 A1 | 12/2009 | Coe et al. | |
| 2009/0326648 A1 | 12/2009 | Machold et al. | |
| 2010/0001038 A1 | 1/2010 | Levin et al. | |
| 2010/0010538 A1* | 1/2010 | Juravic | A61F 2/2481 606/228 |
| 2010/0023118 A1 | 1/2010 | Medlock et al. | |
| 2010/0030014 A1 | 2/2010 | Ferrazzi | |
| 2010/0030328 A1 | 2/2010 | Seguin et al. | |
| 2010/0042147 A1 | 2/2010 | Janovsky et al. | |
| 2010/0063542 A1 | 3/2010 | van der Burg et al. | |
| 2010/0063550 A1 | 3/2010 | Felix et al. | |
| 2010/0076499 A1 | 3/2010 | McNamara et al. | |
| 2010/0094248 A1 | 4/2010 | Nguyen et al. | |
| 2010/0106141 A1 | 4/2010 | Osypka et al. | |
| 2010/0114180 A1 | 5/2010 | Rock et al. | |
| 2010/0121349 A1 | 5/2010 | Meier et al. | |
| 2010/0121435 A1 | 5/2010 | Subrarnanian et al. | |
| 2010/0121437 A1 | 5/2010 | Subrarnanian et al. | |
| 2010/0130989 A1 | 5/2010 | Bourque et al. | |
| 2010/0130992 A1 | 5/2010 | Machold et al. | |
| 2010/0152845 A1 | 6/2010 | Bloom et al. | |
| 2010/0161042 A1* | 6/2010 | Maisano | A61F 2/2457 623/2.11 |
| 2010/0161043 A1 | 6/2010 | Maisano et al. | |
| 2010/0161047 A1* | 6/2010 | Cabiri | A61B 17/072 623/2.37 |
| 2010/0168845 A1 | 7/2010 | Wright | |
| 2010/0174358 A1 | 7/2010 | Rabkin et al. | |
| 2010/0179574 A1 | 7/2010 | Longoria et al. | |
| 2010/0217184 A1 | 8/2010 | Koblish et al. | |
| 2010/0217382 A1 | 8/2010 | Chau et al. | |
| 2010/0234935 A1 | 9/2010 | Bashiri et al. | |
| 2010/0249497 A1 | 9/2010 | Peine et al. | |
| 2010/0249908 A1 | 9/2010 | Chau et al. | |
| 2010/0249915 A1 | 9/2010 | Zhang | |
| 2010/0249920 A1 | 9/2010 | Bolling et al. | |
| 2010/0262232 A1 | 10/2010 | Annest | |
| 2010/0262233 A1 | 10/2010 | He | |
| 2010/0286628 A1 | 11/2010 | Gross | |
| 2010/0286767 A1* | 11/2010 | Zipory | A61F 2/2442 623/2.11 |
| 2010/0298929 A1 | 11/2010 | Thornton et al. | |
| 2010/0305475 A1 | 12/2010 | Hinchliffe et al. | |
| 2010/0324598 A1 | 12/2010 | Anderson | |
| 2011/0004210 A1 | 1/2011 | Johnson et al. | |
| 2011/0004298 A1 | 1/2011 | Lee et al. | |
| 2011/0009956 A1 | 1/2011 | Cartledge et al. | |
| 2011/0011917 A1 | 1/2011 | Loulmet | |
| 2011/0026208 A1 | 2/2011 | Utsuro et al. | |
| 2011/0029066 A1 | 2/2011 | Giiad et al. | |
| 2011/0035000 A1 | 2/2011 | Nieminen et al. | |
| 2011/0066231 A1 | 3/2011 | Cartledge et al. | |
| 2011/0067770 A1 | 3/2011 | Pederson et al. | |
| 2011/0071626 A1 | 3/2011 | Wright et al. | |
| 2011/0082538 A1 | 4/2011 | Dahlgren et al. | |
| 2011/0087146 A1 | 4/2011 | Ryan et al. | |
| 2011/0093002 A1 | 4/2011 | Rucker et al. | |
| 2011/0118832 A1 | 5/2011 | Punjabi | |
| 2011/0137410 A1 | 6/2011 | Hacohen | |
| 2011/0144703 A1 | 6/2011 | Krause et al. | |
| 2011/0202130 A1 | 8/2011 | Cartledge et al. | |
| 2011/0208283 A1 | 8/2011 | Rust | |
| 2011/0230941 A1 | 9/2011 | Markus | |
| 2011/0230961 A1 | 9/2011 | Langer et al. | |
| 2011/0238088 A1 | 9/2011 | Bolduc et al. | |
| 2011/0257433 A1 | 10/2011 | Walker | |
| 2011/0257633 A1 | 10/2011 | Cartledge et al. | |
| 2011/0264208 A1 | 10/2011 | Duffy et al. | |
| 2011/0276062 A1 | 11/2011 | Bolduc | |
| 2011/0288435 A1 | 11/2011 | Christy et al. | |
| 2011/0288635 A1* | 11/2011 | Miller | A61B 17/0401 623/2.1 |
| 2011/0301498 A1 | 12/2011 | Maenriout et al. | |
| 2012/0022557 A1* | 1/2012 | Cabiri | A61B 17/064 606/139 |
| 2012/0022644 A1* | 1/2012 | Reich | A61B 17/068 623/2.37 |
| 2012/0053628 A1 | 3/2012 | Sojka et al. | |
| 2012/0078355 A1 | 3/2012 | Zipory et al. | |
| 2012/0078359 A1 | 3/2012 | Li et al. | |

(56) References Cited

U.S. PATENT DOCUMENTS

| | | | |
|---|---|---|---|
| 2012/0083806 A1* | 4/2012 | Goertzen | A61B 17/064 606/151 |
| 2012/0089022 A1 | 4/2012 | House et al. | |
| 2012/0089125 A1 | 4/2012 | Scheibe et al. | |
| 2012/0095552 A1 | 4/2012 | Spence et al. | |
| 2012/0109155 A1 | 5/2012 | Robinson et al. | |
| 2012/0150290 A1 | 6/2012 | Gabbay | |
| 2012/0158021 A1 | 6/2012 | Morrill | |
| 2012/0179086 A1 | 7/2012 | Shank et al. | |
| 2012/0191182 A1 | 7/2012 | Hauser et al. | |
| 2012/0203332 A1* | 8/2012 | Navia | A61F 2/2445 623/2.11 |
| 2012/0226349 A1 | 9/2012 | Tuval et al. | |
| 2012/0239142 A1 | 9/2012 | Liu et al. | |
| 2012/0245604 A1 | 9/2012 | Tegzes | |
| 2012/0271198 A1 | 10/2012 | Whittaker et al. | |
| 2012/0283757 A1* | 11/2012 | Miller | A61B 17/068 606/151 |
| 2012/0296349 A1 | 11/2012 | Smith et al. | |
| 2012/0296417 A1 | 11/2012 | Hill et al. | |
| 2012/0310330 A1 | 12/2012 | Buchbinder et al. | |
| 2012/0323313 A1 | 12/2012 | Seguin | |
| 2013/0030522 A1 | 1/2013 | Rowe et al. | |
| 2013/0046373 A1 | 2/2013 | Cartledge et al. | |
| 2013/0053884 A1 | 2/2013 | Roorda | |
| 2013/0079873 A1 | 3/2013 | Migliazza et al. | |
| 2013/0085529 A1 | 4/2013 | Housman | |
| 2013/0090724 A1 | 4/2013 | Subramanian et al. | |
| 2013/0096672 A1* | 4/2013 | Reich | A61F 2/2445 623/2.11 |
| 2013/0096673 A1 | 4/2013 | Hill et al. | |
| 2013/0116776 A1 | 5/2013 | Gross et al. | |
| 2013/0123910 A1 | 5/2013 | Cartledge et al. | |
| 2013/0131791 A1 | 5/2013 | Hlavka et al. | |
| 2013/0166017 A1 | 6/2013 | Cartledge et al. | |
| 2013/0190863 A1 | 7/2013 | Call et al. | |
| 2013/0204361 A1 | 8/2013 | Adams et al. | |
| 2013/0226289 A1 | 8/2013 | Shaolian et al. | |
| 2013/0226290 A1 | 8/2013 | Yellin et al. | |
| 2013/0268069 A1 | 10/2013 | Zakai et al. | |
| 2013/0282059 A1 | 10/2013 | Ketai et al. | |
| 2013/0289718 A1 | 10/2013 | Tsukashima et al. | |
| 2013/0297013 A1 | 11/2013 | Klima et al. | |
| 2013/0304093 A1 | 11/2013 | Serina et al. | |
| 2013/0331930 A1 | 12/2013 | Rowe et al. | |
| 2014/0067054 A1 | 3/2014 | Chau et al. | |
| 2014/0081394 A1 | 3/2014 | Keranen et al. | |
| 2014/0088368 A1 | 3/2014 | Park | |
| 2014/0088646 A1 | 3/2014 | Wales et al. | |
| 2014/0094826 A1 | 4/2014 | Sutherland et al. | |
| 2014/0094903 A1 | 4/2014 | Miller et al. | |
| 2014/0094906 A1 | 4/2014 | Spence et al. | |
| 2014/0114390 A1 | 4/2014 | Tobis et al. | |
| 2014/0135799 A1 | 5/2014 | Henderson | |
| 2014/0142619 A1 | 5/2014 | Serina et al. | |
| 2014/0142695 A1 | 5/2014 | Gross et al. | |
| 2014/0148849 A1 | 5/2014 | Serina et al. | |
| 2014/0155783 A1 | 6/2014 | Starksen et al. | |
| 2014/0163670 A1 | 6/2014 | Alon et al. | |
| 2014/0163690 A1 | 6/2014 | White | |
| 2014/0188108 A1 | 7/2014 | Goodine et al. | |
| 2014/0188140 A1 | 7/2014 | Meier et al. | |
| 2014/0188215 A1 | 7/2014 | Hlavka et al. | |
| 2014/0194976 A1 | 7/2014 | Starksen et al. | |
| 2014/0207231 A1 | 7/2014 | Hacohen et al. | |
| 2014/0243659 A1 | 8/2014 | Robinson | |
| 2014/0243894 A1 | 8/2014 | Groothuis et al. | |
| 2014/0243963 A1* | 8/2014 | Sheps | A61B 90/50 623/2.11 |
| 2014/0251042 A1 | 9/2014 | Asselin et al. | |
| 2014/0275757 A1 | 9/2014 | Goodwin et al. | |
| 2014/0276648 A1 | 9/2014 | Hammer et al. | |
| 2014/0296962 A1 | 10/2014 | Cartledge et al. | |
| 2014/0303649 A1 | 10/2014 | Nguyen et al. | |
| 2014/0303720 A1 | 10/2014 | Sugimoto et al. | |
| 2014/0309661 A1 | 10/2014 | Sheps et al. | |
| 2014/0309730 A1* | 10/2014 | Alon | A61F 2/2445 623/2.11 |
| 2014/0343668 A1 | 11/2014 | Zipory et al. | |
| 2014/0350660 A1 | 11/2014 | Cocks et al. | |
| 2014/0379006 A1 | 12/2014 | Sutherland et al. | |
| 2015/0018940 A1 | 1/2015 | Quill et al. | |
| 2015/0051697 A1 | 2/2015 | Spence et al. | |
| 2015/0081014 A1 | 3/2015 | Gross et al. | |
| 2015/0094800 A1 | 4/2015 | Chawla | |
| 2015/0100116 A1 | 4/2015 | Mohl et al. | |
| 2015/0112432 A1 | 4/2015 | Reich et al. | |
| 2015/0127097 A1 | 5/2015 | Neumann et al. | |
| 2015/0133997 A1 | 5/2015 | Deitch et al. | |
| 2015/0182336 A1 | 7/2015 | Zipory et al. | |
| 2015/0230919 A1 | 8/2015 | Chau et al. | |
| 2015/0272586 A1 | 10/2015 | Herman et al. | |
| 2015/0272734 A1 | 10/2015 | Sheps et al. | |
| 2015/0282931 A1 | 10/2015 | Brunnett et al. | |
| 2015/0351910 A1 | 12/2015 | Gilmore et al. | |
| 2016/0008132 A1 | 1/2016 | Cabiri et al. | |
| 2016/0058557 A1 | 3/2016 | Reich et al. | |
| 2016/0113767 A1 | 4/2016 | Miller et al. | |
| 2016/0120642 A1 | 5/2016 | Shaolian et al. | |
| 2016/0120645 A1 | 5/2016 | Alon | |
| 2016/0158008 A1 | 6/2016 | Miller et al. | |
| 2016/0242762 A1 | 8/2016 | Gilmore et al. | |
| 2016/0262755 A1 | 9/2016 | Zipory et al. | |
| 2016/0302917 A1 | 10/2016 | Schewel | |
| 2016/0317302 A1 | 11/2016 | Madjarov et al. | |
| 2016/0361058 A1 | 12/2016 | Bolduc et al. | |
| 2016/0361168 A1 | 12/2016 | Gross et al. | |
| 2016/0361169 A1 | 12/2016 | Gross et al. | |
| 2017/0000609 A1 | 1/2017 | Gross et al. | |
| 2017/0042670 A1 | 2/2017 | Shaolian et al. | |
| 2017/0224489 A1 | 8/2017 | Starksen et al. | |
| 2017/0245993 A1 | 8/2017 | Gross et al. | |
| 2018/0008409 A1 | 1/2018 | Kutzik et al. | |
| 2018/0049875 A1 | 2/2018 | Iflah et al. | |
| 2018/0168803 A1 | 6/2018 | Pesce et al. | |
| 2018/0289480 A1 | 10/2018 | D'arnbra et al. | |
| 2018/0318080 A1 | 11/2018 | Quill et al. | |
| 2018/0318083 A1 | 11/2018 | Bolling et al. | |
| 2019/0029498 A1 | 1/2019 | Mankowski et al. | |
| 2019/0038411 A1 | 2/2019 | Alon | |
| 2019/0111239 A1 | 4/2019 | Bolduc et al. | |
| 2019/0117400 A1 | 4/2019 | Medema et al. | |
| 2019/0125325 A1 | 5/2019 | Sheps et al. | |
| 2019/0151093 A1 | 5/2019 | Keidar et al. | |
| 2019/0175346 A1 | 6/2019 | Schaffner et al. | |
| 2019/0183648 A1 | 6/2019 | Trapp et al. | |
| 2019/0290260 A1 | 9/2019 | Caffes et al. | |
| 2019/0290431 A1 | 9/2019 | Genovese et al. | |
| 2019/0343633 A1 | 11/2019 | Garvin et al. | |

FOREIGN PATENT DOCUMENTS

| | | | |
|---|---|---|---|
| WO | 9205093 A1 | 4/1992 | |
| WO | 9846149 A1 | 10/1998 | |
| WO | WO-0158364 A1 * | 8/2001 | A61B 17/064 |
| WO | 02085250 A3 | 2/2003 | |
| WO | 03047467 A1 | 6/2003 | |
| WO | 2010000454 A1 | 1/2010 | |
| WO | 2012176195 A3 | 3/2013 | |
| WO | 2014064964 A1 | 5/2014 | |
| WO | 2019145941 A1 | 8/2019 | |
| WO | 2019145947 A1 | 8/2019 | |
| WO | 2019182645 A1 | 11/2019 | |
| WO | 2019224814 A1 | 11/2019 | |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.

(56) References Cited

OTHER PUBLICATIONS

Ahmadi, Ali et al. "Percutaneously adjustable pulmonary artery band." The Annals of thoracic surgery 60 (1995): S520-S522.
Alfieri et al., "An effective technique to correct anterior mitral leaflet prolapse," J Card 14(6):468-470 (1999).
Alfieri et al., "The double orifice technique in mitral valve repair: a simple solution for complex problems," Journal of Thoracic Cardiovascular Surgery 122:674-681 (2001).
Alfieri et al., "The edge to edge technique," The European Association for Cardio-Thoracic Surgery 14th Annual Meeting Oct. 7-11, Book of Procees. (2000).
Alfieri et al."Novel Suture Device for Beating-Heart Mitral Leaflet Approximation", Ann Thorac Surg. 2002, 74:1488-1493.
Alfieri, "The edge-to-edge repair of the mitral valve," [Abstract] 6th Annual NewEra Cardiac Care: Innovation & Technology, Heart Surgery Forum pp. 103. (2000).
Amplatzer Cardiac Plug brochure (English pages), AGA Medical Corporation (Plymouth, MN) (copyright 2008-2010, downloaded Jan. 11, 2011).
AMPLATZER® Cribriforrn Occluder. A patient guide to Percutaneous, Transcatheter, Atrial Septal Defect Closuer. AGA Medical Corporation, Apr. 2008.
AMPLATZER® Septal Occluder. A patient guide to the Non-Surgical Closuer of the Atrial Septal Defect Using the AMPLATZER Septal Occluder System, AGA Medical Corporation, Apr. 2008.
Assad, Renato S. "Adjustable Pulmonary Artery Banding." (2014).
Brennan, Jennifer, 510(k) Summary of safety and effectiveness, Jan. 2008.
Daebritz, S. et al. "Experience with an adjustable pulmonary artery banding device in two cases: initial success-midterm failure." The Thoracic and cardiovascular surgeon 47.01 (1999): 51-52.
Dang NC et al. "Simplified Placement of Multiple Artificial Mitral Valve Chords," The Heart Surgery Forum #2005-1005, 8 (3) (2005).
Dictionary.com definition of "lock", Jul. 29, 2013.
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
Elliott, Daniel S., Gerald W. Timm, and David M. Barrett. "An implantable mechanical urinary sphincter: a new nonhydraulic design concept." Urology52.6 (1998): 1151-1154.
Langer et al. Ring plus String: Papillary muscle repositioning as an adjunctive repair technique for ischemic mitral regurgitation, The Journal of Thoracic Cardiovascular surgery vol. 133 No. 1, Jan. 2007.
Langer et al. RING+STRING, Successful Repair technique for ischemic mitral regurgitation with severe leaflet Tethering, The Department of Thoracic Cardiovascular surgery, Hamburg, Germany, Nov. 2008.
Maisano, The double-orifice technique as a standardized approach to treat mitral . . . , European Journal of Cardio-thoracic Surgery 17 (2000) 201-205.
Odell JA et al., "Early Results o4yf a Simplified Method of Mitral Valve Annuloplasty," Circulation 92:150-154 (1995).
O'Reilly S et al., "Heart valve surgery pushes the envelope," Medtech Insight 8(3): 73, 99-108 (2006).
Park, Sang C. et al. "A percutaneously adjustable device for banding of the pulmonary trunk." International journal of cardiology 9.4 (1985): 477-484.
Swain CP et al., "An endoscopically deliverable tissue-transfixing device for securing biosensors in the gastrointestinal tract," Gastrointestinal Endoscopy 40(6): 730-734 (1994).
Swenson, O. An experimental implantable urinary sphincter. Invest Urol. Sep. 1976;14(2):100-3.
Swenson, O. and Malinin, T.I., 1978. An improved mechanical device for control of urinary incontinence. Investigative urology, 15(5), pp. 389-391.
Swenson, Orvar. "Internal device for control of urinary incontinence," Journal of pediatric surgery 7.5 (1972): 542-545.
Tajik, Abdul, "Two dimensional real-time ultrasonic imaging of the heart and great vessels", Mayo Clin Proc. vol. 53:271-303, 1978.

* cited by examiner

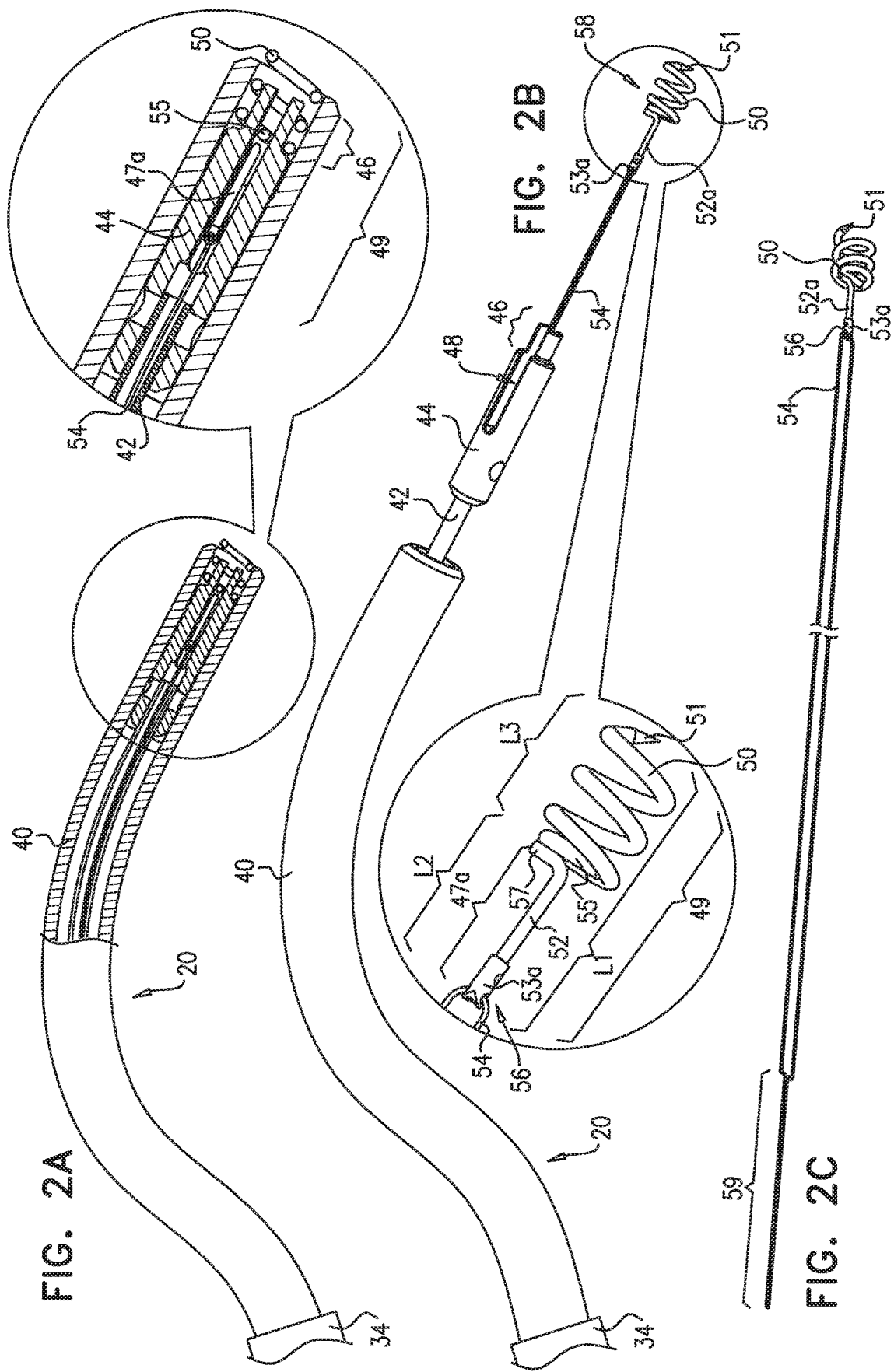

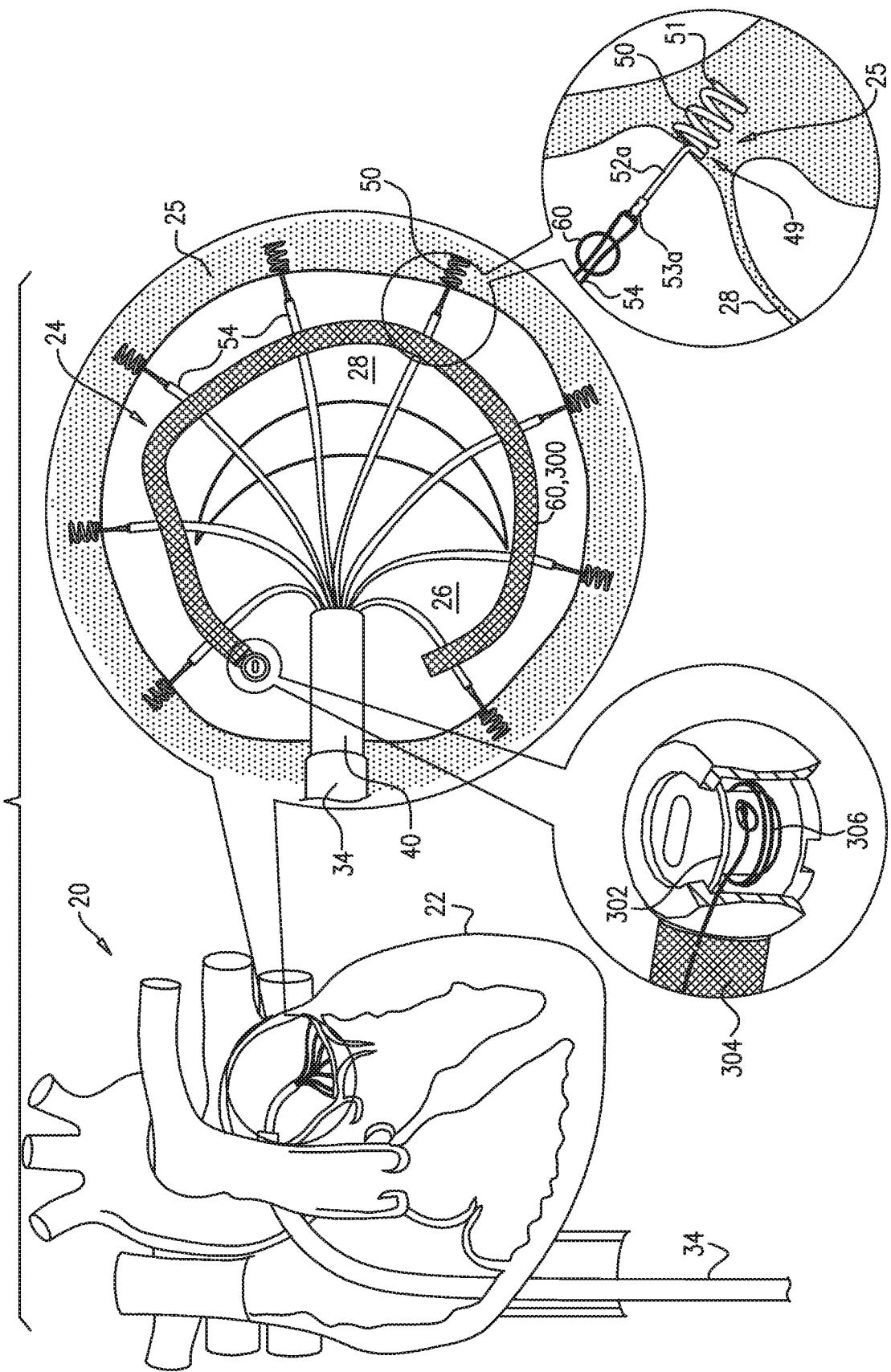

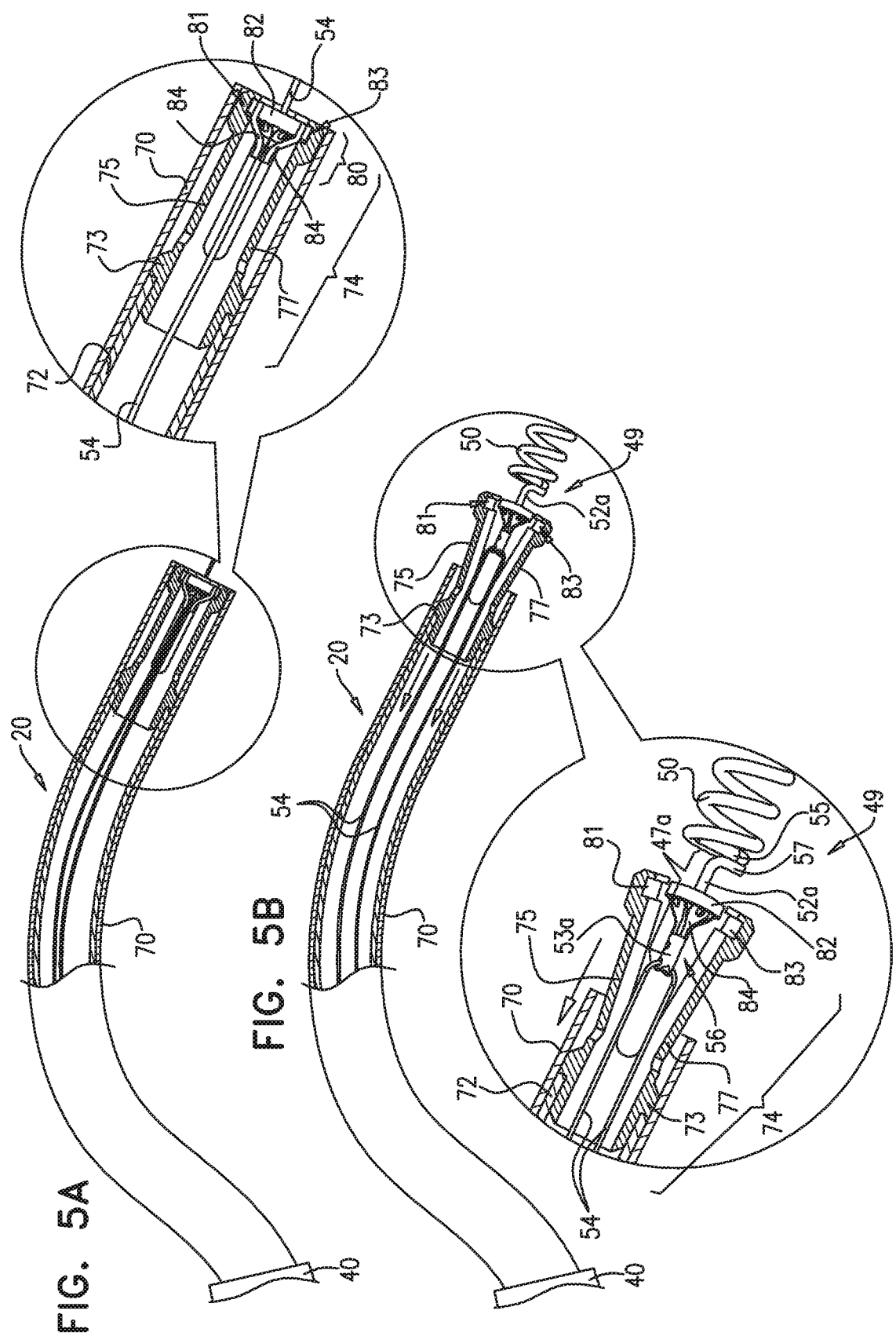

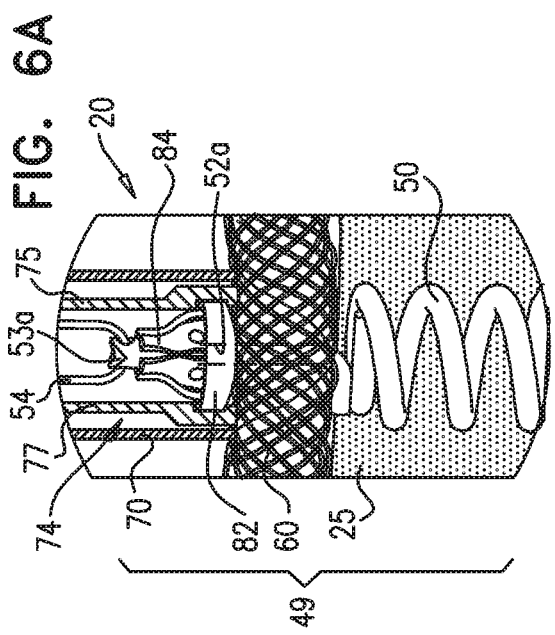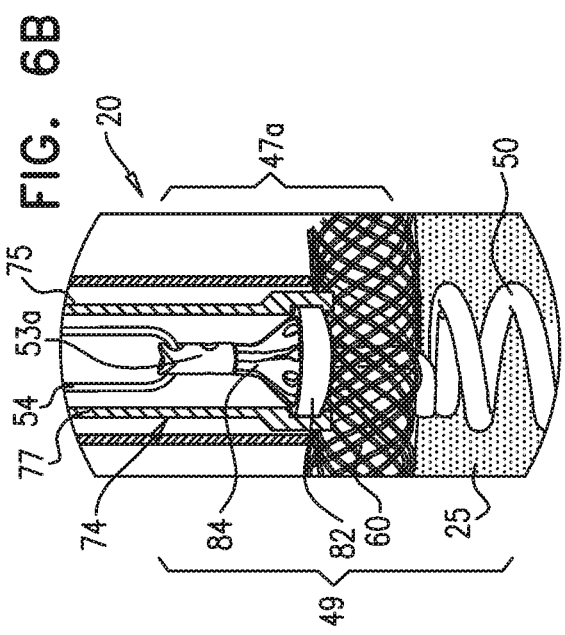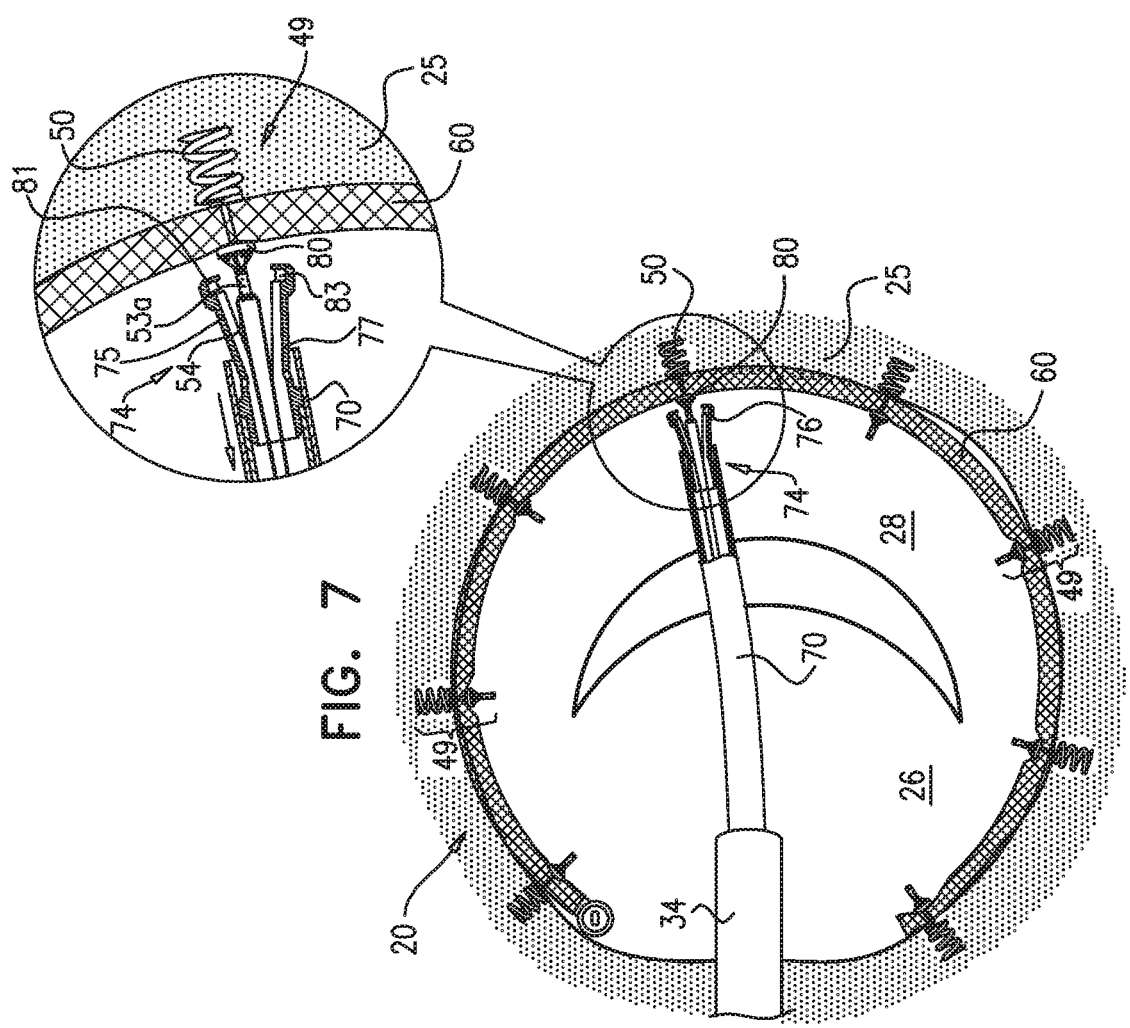

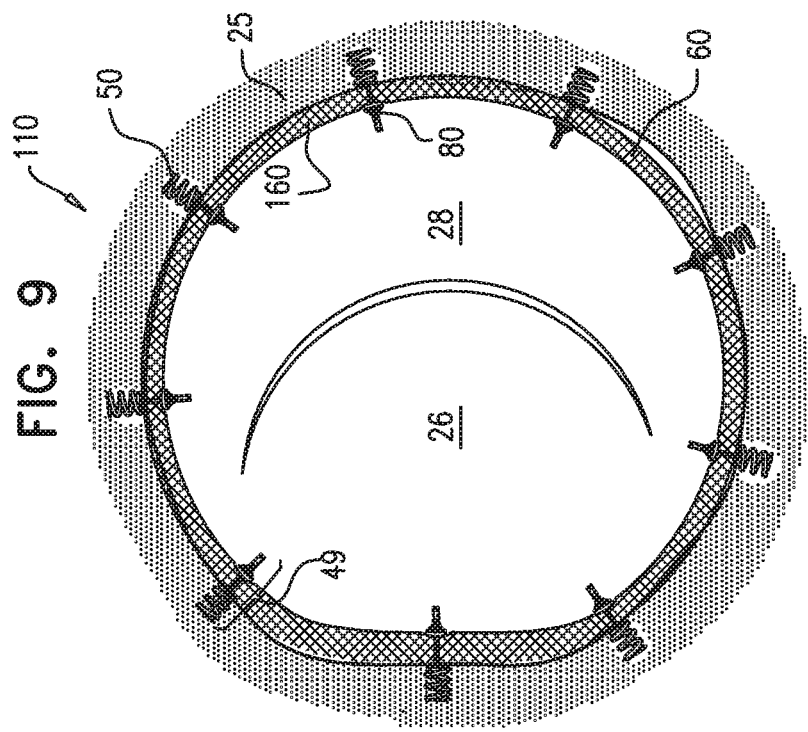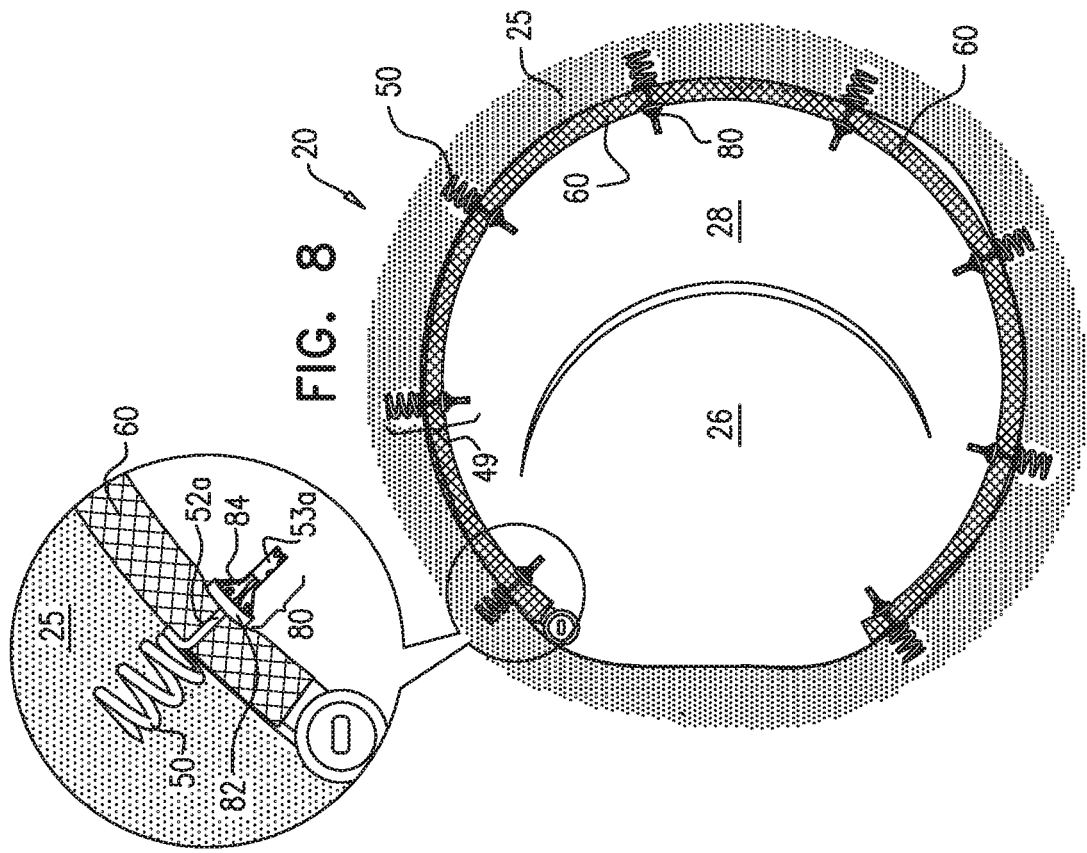

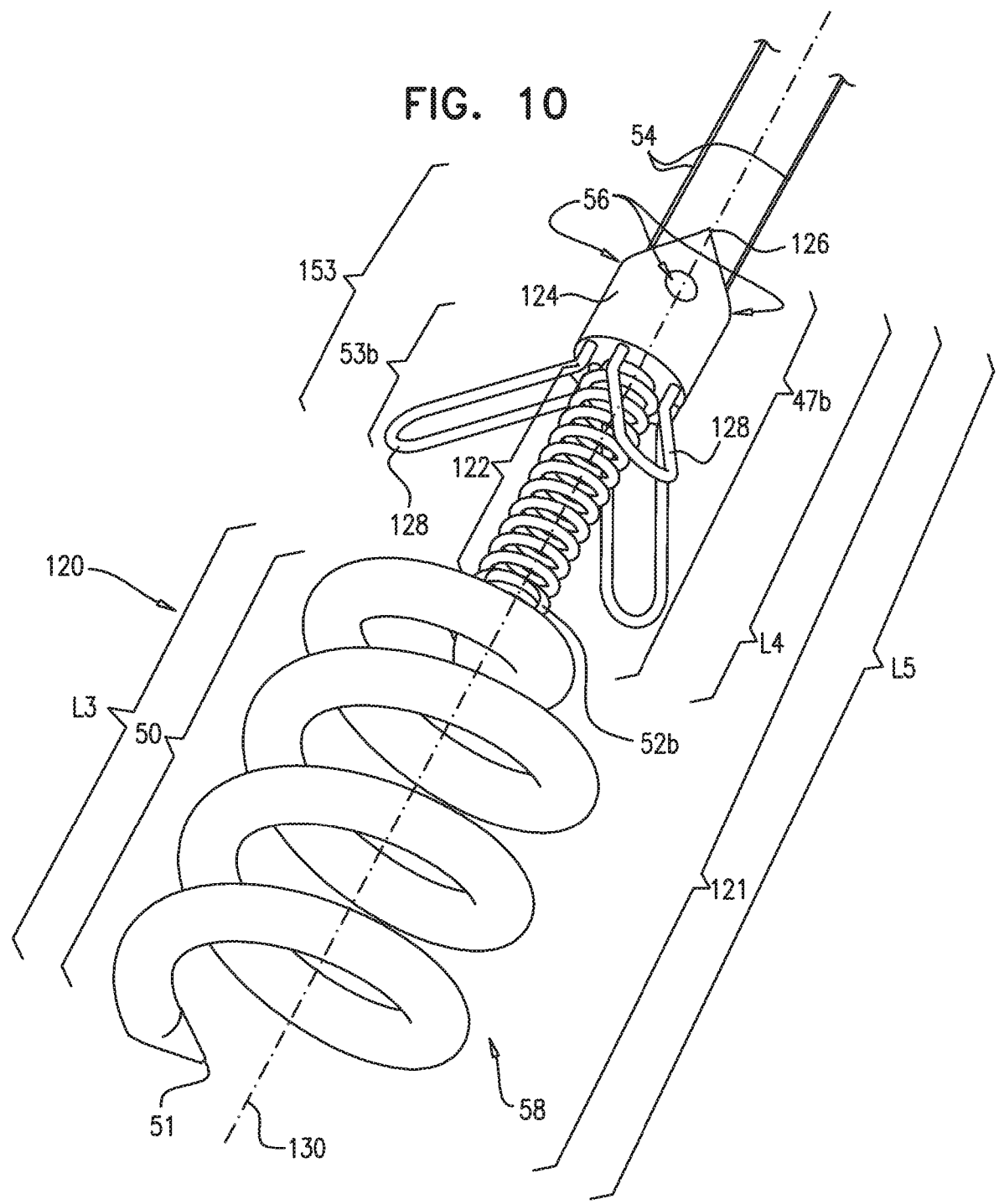

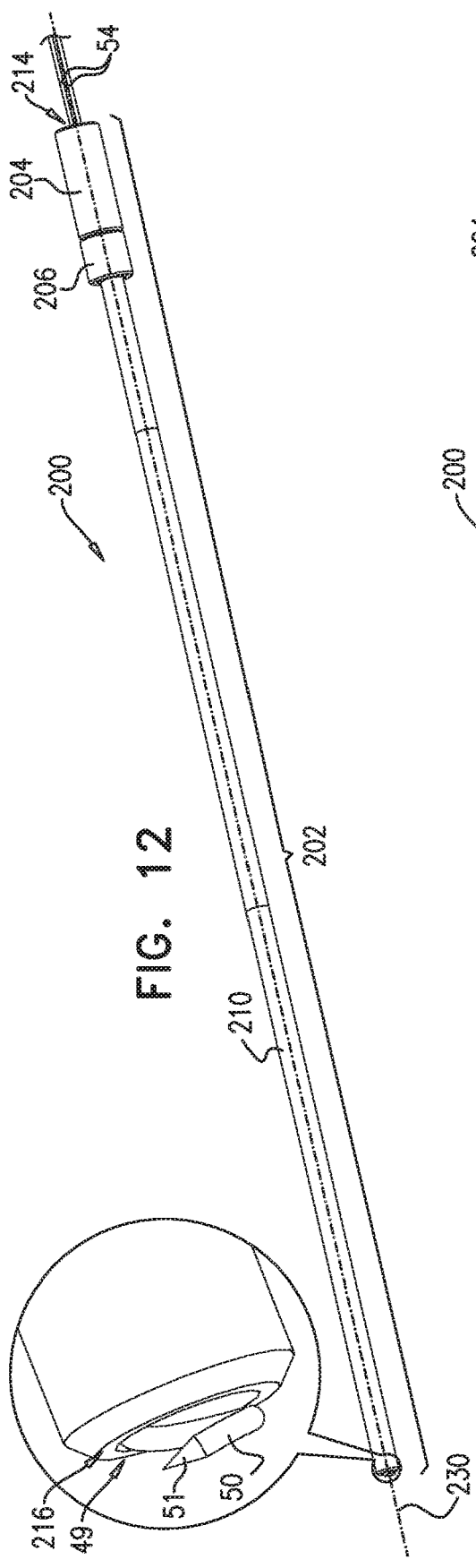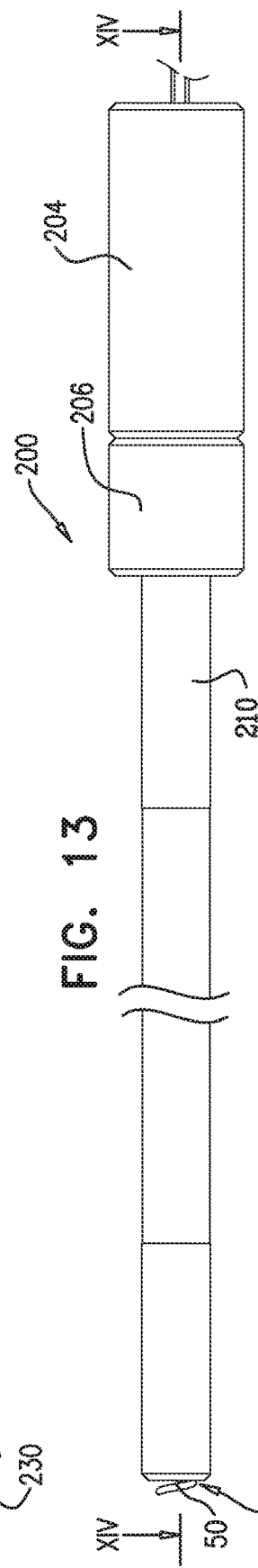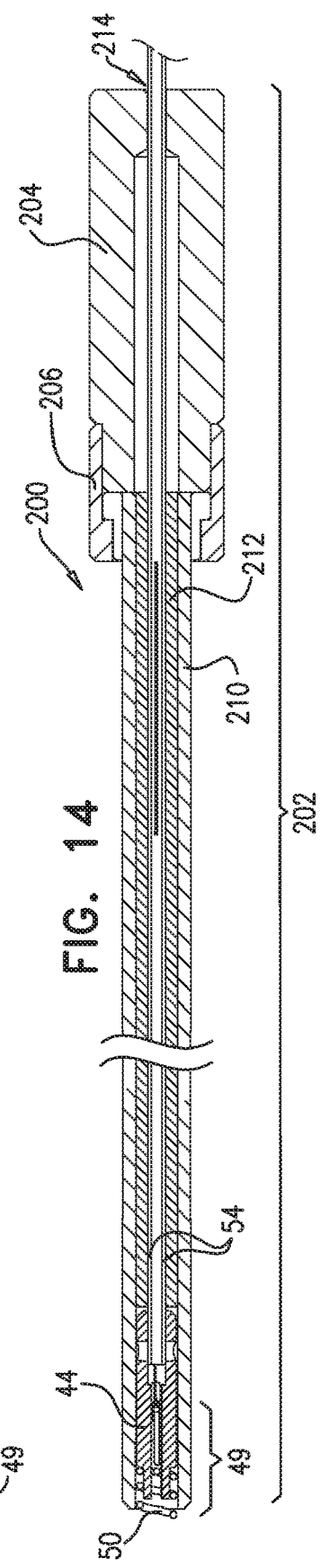

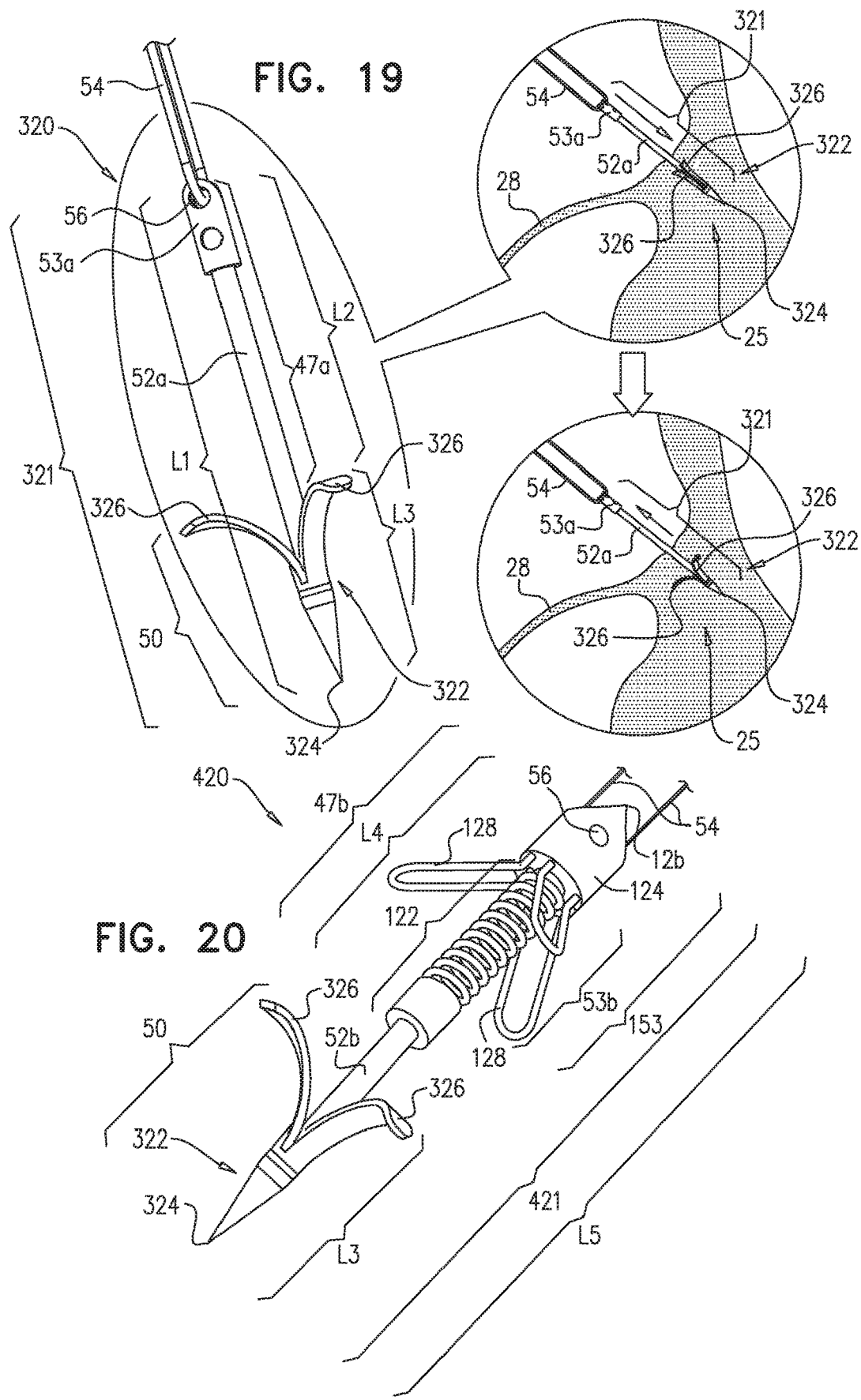

TISSUE ANCHOR FOR ANNULOPLASTY DEVICE

CROSS-REFERENCES TO RELATED APPLICATIONS

The present application is a continuation application of U.S. patent application Ser. No. 15/208,253 to Miller et al., entitled, "Tissue anchor for annuloplasty device," filed on Jul. 12, 2016, which published as US 2018/0014933 and which is a continuation application of U.S. patent application Ser. No. 14/667,090 to Miller et al., entitled, "Tissue anchor for annuloplasty device," filed on Mar. 24, 2015, which issued as U.S. Pat. No. 9,414,921, and which is a continuation application of U.S. patent application Ser. No. 13/504,870 to Miller et al., entitled, "Tissue anchor for annuloplasty device," filed on Jul. 19, 2012, which issued as U.S. Pat. No. 9,011,520, and which is a US national phase application of PCT/IL2010/000890 to Miller et al., entitled, "Tissue anchor for annuloplasty device," filed on Oct. 28, 2010, which published as WO 2011/051942, and which claims priority from and is a continuation-in-part of U.S. patent application Ser. No. 12/608,316 to Miller et al., entitled, "Tissue anchor for annuloplasty device," filed on Oct. 29, 2009, which issued as U.S. Pat. No. 8,277,502. All of these applications and patents are assigned to the assignee of the present application and are incorporated herein by reference.

FIELD OF THE INVENTION

Some applications of the present invention relate in general to tissue anchors. More specifically, some applications of the present invention relate to tissue anchors for repair of an atrioventricular valve of a patient.

BACKGROUND OF THE INVENTION

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

US Patent Application 2004/0236419 to Milo describes methods for reconfiguring an atrioventricular heart valve that may use systems comprising a partial or complete annuloplasty rings proportioned to reconfigure a heart valve that has become in some way incompetent, a pair of trigonal sutures or implantable anchors, and a plurality of staples which may have pairs of legs that are sized and shaped for association with the ring at spaced locations along its length. These systems permit relative axial movement between the staples and the ring, whereby a patient's heart valve can be reconfigured in a manner that does not deter subtle shifting of the native valve components. Shape-memory alloy material staples may have legs with free ends that interlock following implantation. Annuloplasty rings may be complete or partial and may be fenestrated. One alternative method routes a flexible wire, preferably of shape-memory material, through the bights of pre-implanted staples. Other alternative systems use linkers of shape-memory material having hooked ends to interengage with staples or other implanted supports which, following implantation, decrease in effective length and pull the staples or other supports toward one another so as to create desired curvature of the reconfigured valve. These linkers may be separate from the supports or may be integral with them and may have a variety of shapes and forms. Various of these systems may be implanted non-invasively using a delivery catheter.

US 2007/0049942 to Hindrichs et al. describes remodeling a soft body tissue structure by shortening the distance between first and second portions of that tissue structure. First and second anchor structures are respectively implanted in the first and second portions of the tissue structure. These anchor structures are linked by a linking structure, the length of which between the anchor structures can be shortened to pull the tissue structure portions toward one another. Each of the anchor structures may include two screw structures that are driven into the associated tissue structure portion transverse to the linking structure and with a spacer between the two screws. The entire prosthesis can be implanted percutaneously if desired. An illustrative use of the prosthesis is to shorten the annulus of a patient's mitral valve, with at least a portion of the prosthesis implanted in the patient's coronary sinus.

The following patents and patent application publications may be of interest:
PCT Publication WO 07/136783 to Cartledge et al.
PCT Publication WO 08/068756 to Gross et al.
PCT Publication WO 10/004546 to Gross et al.
PCT Publication WO 10/073246 to Cabiri et al.
U.S. Pat. No. 5,306,296 to Wright et al.
U.S. Pat. No. 6,569,198 to Wilson et al.
U.S. Pat. No. 6,619,291 to Hlavka et al.
U.S. Pat. No. 6,764,510 to Vidlund et al.
U.S. Pat. No. 7,004,176 to Lau
U.S. Pat. No. 7,101,395 to Tremulis et al.
U.S. Pat. No. 7,175,660 to Cartledge et al.
US 2003/0050693 to Quijano et al
US 2003/0167062 to Gambale et al.
US 2004/0024451 to Johnson et al.
US 2004/0148021 to Cartledge et al.
US 2005/0171601 to Cosgrove et al.
US 2005/0288781 to Moaddeb et al.
US 2007/0016287 to Cartledge et al.
US 2007/0080188 to Spence et al.
US 2007/0219558 to Deutsch
US 2007/0282375 to Hindrichs et al.
US 2008/0262609 to Gross et al.
US 2010/0161041 to Maisano et al.
US 2010/0161042 to Maisano et al.
US 2010/0211166 to Miller et al.

The following articles may be of interest:
O'Reilly S et al., "Heart valve surgery pushes the envelope," Medtech Insight 8(3): 73, 99-108 (2006)
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003)

SUMMARY OF THE INVENTION

In some applications of the present invention, a tissue anchor is provided that is configured for receiving an implant and facilitating implantation of the implant. The anchor comprises a distal tissue coupling element, e.g., a helical anchor, which penetrates tissue of a patient. The anchor also comprises a proximal implant-penetrating element which receives and facilitates coupling of the implant to the tissue anchor. The implant-penetrating element comprises a post, which extends between the proximal tip and the proximal end of the distal tissue coupling element. For some applications, the proximal tip of the implant-penetrating element comprises a barb which punctures and receives the implant.

Typically, during an open-heart, minimally-invasive, or transcatheter procedure, a plurality of tissue anchors are implanted along an annulus of an atrioventricular valve of the patient, and are configured to receive and facilitate implantation of a valve-repair implant, e.g., an annuloplasty ring or a prosthetic valve. Each anchor is reversibly coupled to a cord, e.g., a suture or a wire, at a proximal end of the implant-penetrating element. Prior to implantation of the valve-repair implant, each cord is threaded through the implant, and the implant is then slid toward the annulus along the cords. In response to continued pushing of the valve-repair implant, the implant is then punctured at respective locations by the proximal tips of each one of the implant-penetrating elements. The physician continues to push the valve-repair implant so that the implant slides along the implant-penetrating elements and the posts of the anchors. The implant is pushed along the post until the proximal tips of each one of the implant-penetrating elements are exposed from within the lumen of the valve-repair implant and disposed proximally to a proximal surface of the implant. The valve-repair implant is then locked in place at the surface of the implant that faces the lumen of the atrium of the patient. Following the locking in place of the implant, the cords are decoupled from the anchors and removed from within the body of the patient.

In some applications of the present invention, a proximal restraining element, e.g., radially-expandable arms, is coupled to a proximal portion of the post of the anchor. This restraining element restrains the implant from separating from the implant-penetrating element.

In some applications of the present invention, an elastic portion, e.g., a tension spring, is coupled at a proximal end to the proximal tip of the implant-penetrating element, and at a distal end to the proximal end of the post.

There is therefore provided, in accordance with some applications of the present invention, apparatus for use with an implant, the apparatus including:
 a tissue anchor, which includes:
  a distal tissue coupling element, which is configured to penetrate cardiac tissue; and
  a proximal implant-penetrating element configured to penetrate the implant, the proximal implant-penetrating element being shaped so as to define a passage therethrough, which passage has at least two openings that are within 1 mm of a proximal end of the implant-penetrating element; and
 a cord configured to be removably passed through the passage.

In some applications of the present invention, the proximal implant-penetrating element includes a post.

In some applications of the present invention, the post has a length of between 1 and 7 mm and a greatest cross-sectional area of between 0.03 mm^2 and 0.2 mm^2, which length is at least 4 times the square root of the greatest cross-sectional area.

In some applications of the present invention, the length of the post is at least 5 times the square root of the greatest cross-sectional area of the post.

In some applications of the present invention, the length of the post is at least 8 times the square root of the greatest cross-sectional area of the post.

In some applications of the present invention, the length of the post is at least 10 times the square root of the greatest cross-sectional area of the post.

In some applications of the present invention, the length of the post is at least 15 times the square root of the greatest cross-sectional area of the post.

In some applications of the present invention, the apparatus further includes a proximal restraining element, which is configured to be coupleable to the post within 2 mm of a proximal end of the post, and which is configured to restrain the implant from separating from the implant-penetrating element.

In some applications of the present invention, the proximal restraining element is shaped so as to define an opening therethrough, through which the cord is configured to pass.

In some applications of the present invention, the post defines a protrusion configured to protrude into a plane of the implant and to couple the implant to the tissue anchor.

In some applications of the present invention, the protrusion is shaped so as to define a distal shelf that has a transverse cross-sectional length that is larger than a transverse cross-sectional length of the implant-receiving element, the distal shelf being configured to facilitate restricting of proximal motion of the implant along the protrusion.

In some applications of the present invention, the proximal restraining element has a greatest cross-sectional area that is at least 1.5 times a greatest cross-sectional area of the post.

In some applications of the present invention, the apparatus further includes a lock configured to be advanced toward the anchor and disposed between the implant and the proximal restraining element, the lock including:
 a distal portion configured to rest against the implant, and
 an expandable proximal portion having a cross-sectional area during a resting state of the lock that is larger than the greatest cross-sectional area of the post and smaller than the greatest cross-sectional area of the proximal restraining element.

In some applications of the present invention, the proximal implant-penetrating element includes a barb configured to restrict proximal movement of the implant along the implant-penetrating element.

In some applications of the present invention, the barb includes a proximal restraining element which is configured to restrain the implant from separating from the implant-penetrating element.

In some applications of the present invention, the barb includes one or more arms that are radially expandable to rest against an external surface of the implant following coupling of the implant to the implant-penetrating element.

In some applications of the present invention, the arms are radially collapsible during at least a portion of the coupling of the implant to the implant-penetrating element.

In some applications of the present invention, the proximal implant-penetrating element includes an elastic portion that is configured to assume a first length when relaxed, and a second, greater length when under load.

In some applications of the present invention, the elastic portion includes a tension spring.

In some applications of the present invention, the proximal implant-penetrating element has a length of between 3 and 5 mm when the elastic portion is relaxed.

In some applications of the present invention, the implant-penetrating element includes a proximal restraining element which is coupled to the post, and which is configured to restrain the implant from separating from the implant-penetrating element.

In some applications of the present invention, the proximal restraining element is coupled within 2 mm of a proximal end of the post.

In some applications of the present invention, the proximal restraining element is shaped so as to define an opening therethrough, through which the cord is configured to pass.

In some applications of the present invention, the proximal restraining element includes a protrusion configured to protrude into a plane of the implant and to couple the implant to the tissue anchor.

In some applications of the present invention, the protrusion is shaped so as to define a distal shelf that has a transverse cross-sectional length that is larger than a transverse cross-sectional length of the implant-receiving element, the distal shelf being configured to facilitate restricting of proximal motion of the implant along the protrusion.

In some applications of the present invention, the proximal restraining element has a greatest cross-sectional area that is at least 1.5 times a greatest cross-sectional area of the post.

In some applications of the present invention, the apparatus further includes a lock configured to be advanced toward the anchor and disposed between the implant and the proximal restraining element, the lock including:

a distal portion configured to rest against the implant, and an expandable proximal portion having a cross-sectional area during a resting state of the lock that is larger than the greatest cross-sectional area of the post and smaller than the greatest cross-sectional area of the proximal restraining element.

In the proximal restraining element includes a barb configured to restrict proximal movement of the implant along the implant-penetrating element.

In some applications of the present invention, the barb includes one or more arms that are radially expandable to rest against an external surface of the implant following coupling of the implant to the implant-penetrating element.

In some applications of the present invention, the arms are radially collapsible during at least a portion of the coupling of the implant to the implant-penetrating element.

In some applications of the present invention, the proximal implant-penetrating element includes an elastic portion that is configured to assume a first length when relaxed, and a second, greater length when under load.

In some applications of the present invention, the elastic portion includes a tension spring.

In some applications of the present invention, the proximal implant-penetrating element has a length of between 3 and 5 mm when the elastic portion is relaxed.

In some applications of the present invention, the coupling element is shaped so as to define a shape selected from the group consisting of: a helix, a spiral, and a screw shaft.

In some applications of the present invention, the coupling element is shaped so as to define one or more radially-expandable prongs, the prongs being configured to expand and facilitate anchoring of the coupling element and restrict proximal motion of the tissue anchor.

In some applications of the present invention, the apparatus further includes the implant, the post is configured to couple the implant to the anchor.

In some applications of the present invention, the implant includes an annuloplasty device.

In some applications of the present invention, the annuloplasty device includes:

a sleeve having a lumen;

a spool coupled to the sleeve; and a flexible contracting member that is coupled to the spool and the sleeve, such that winding the contracting member around the spool tightens the device.

In some applications of the present invention, the distal tissue coupling element and the proximal implant-penetrating element include respective elements that are coupled to one another.

In some applications of the present invention, the distal tissue coupling element and the proximal implant-penetrating element are fabricated from a single piece.

There is additionally provided, in accordance with some applications of the present invention apparatus, including:

a tissue-repair implant configured to reside chronically in a heart of a patient;

a tissue anchor including:

a distal tissue coupling element configured to couple the tissue anchor to tissue of the heart of the patient; and a proximal implant-receiving element configured to receive at least a portion of the tissue-repair implant and facilitate coupling of the tissue-repair implant to the tissue anchor, the proximal implant-receiving element including:

a proximal implant-restraining element coupled to a proximal portion of the implant-receiving element, the proximal implant-restraining element being configured to restrain the implant from separating from the implant-receiving element.

In some applications of the present invention, the proximal restraining element includes a protrusion configured to protrude into a plane of the implant and to couple the implant to the tissue anchor.

In some applications of the present invention, the protrusion is shaped so as to define a distal shelf that has a transverse cross-sectional length that is larger than a transverse cross-sectional length of the implant-receiving element, the distal shelf being configured to facilitate restricting of proximal motion of the implant along the protrusion.

In some applications of the present invention, the apparatus further includes a cord removably couplable to the tissue anchor, the cord being configured to facilitate passage of the implant therealong and toward the tissue anchor.

In some applications of the present invention, the cord passes through a portion of the implant-receiving element.

In some applications of the present invention, the proximal implant-receiving element includes a post.

In some applications of the present invention, the post has a length of between 1 and 7 mm and a greatest cross-sectional area of between 0.03 mm^2 and 0.2 mm^2, which length is at least 4 times the square root of the greatest cross-sectional area.

In some applications of the present invention, the length of the post is at least 5 times the square root of the greatest cross-sectional area of the post.

In some applications of the present invention, the length of the post is at least 8 times the square root of the greatest cross-sectional area of the post.

In some applications of the present invention, the length of the post is at least 10 times the square root of the greatest cross-sectional area of the post.

In some applications of the present invention, the length of the post is at least 15 times the square root of the greatest cross-sectional area of the post.

In some applications of the present invention, the proximal implant-restraining element is coupled to the post within 2 mm of a proximal end of the post.

In some applications of the present invention, the proximal implant-restraining element is shaped so as to define an opening therethrough, through which the cord is configured to pass.

In some applications of the present invention, the proximal implant-restraining element has a greatest cross-sectional area that is at least 1.5 times a greatest cross-sectional area of the post.

In some applications of the present invention, the apparatus further includes a lock configured to be advanced toward the anchor and disposed between the implant and the proximal implant-restraining element, the lock including:

a distal portion configured to rest against the implant; and
an expandable proximal portion having a cross-sectional area during a resting state of the lock that is larger than the greatest cross-sectional area of the post and smaller than the greatest cross-sectional area of the proximal implant-restraining element.

In some applications of the present invention, the proximal implant-restraining element includes a barb configured to restrict proximal movement of the implant along the implant-receiving element.

In some applications of the present invention, the barb includes one or more arms that are radially expandable to rest against an external surface of the implant following coupling of the implant to the implant-receiving element.

In some applications of the present invention, the arms are radially collapsible during at least a portion of the coupling of the implant to the implant-receiving element.

In some applications of the present invention, the proximal implant-receiving element includes an elastic portion that is configured to assume a first length when relaxed, and a second, greater length when under load.

In some applications of the present invention, the elastic portion includes a tension spring.

In some applications of the present invention, the proximal implant-receiving element has a length of between 3 and 5 mm when the elastic portion is relaxed.

In some applications of the present invention, the distal tissue coupling element is shaped so as to define a shape selected from the group consisting of: a helix, a spiral, and a screw shaft.

In some applications of the present invention, the distal tissue coupling element is shaped so as to define one or more radially-expandable prongs, the prongs being configured to expand and facilitate anchoring of the coupling element and restrict proximal motion of the tissue anchor.

In some applications of the present invention, the apparatus further includes the implant, the implant-receiving element is configured to couple the implant to the anchor.

In some applications of the present invention, the implant includes an annuloplasty device.

In some applications of the present invention, the implant includes:

a spool coupled to the tissue-repair implant; and
a flexible contracting member that is coupled to the spool and the sleeve, such that winding the contracting member around the spool tightens the contracting member.

In some applications of the present invention, the distal tissue coupling element and the proximal implant-receiving element include respective elements that are coupled to one another.

In some applications of the present invention, the distal tissue coupling element and the proximal implant-receiving element are fabricated from a single piece.

There is also provided, in accordance with some applications of the present invention, the following inventive concepts:

1. A method comprising:

coupling, to cardiac tissue of a patient, a distal tissue coupling element of a tissue anchor, which tissue anchor further includes (a) a proximal implant-penetrating element, which is shaped so as to define a passage therethrough, which passage has at least two openings that are within 1 mm of a proximal end of the implant-penetrating element, and (b) a cord, which is removably passed through the passage;

passing the cord through an implant; and
advancing the implant over the cord until the implant reaches and is penetrated by the proximal implant-penetrating element.

2. The method according to inventive concept 1, wherein coupling the distal tissue coupling element comprises:

coupling a distal tissue coupling element that comprises one or more radially-expandable prongs configured to expand and facilitate anchoring of the coupling element, and by the coupling, restricting proximal motion of the tissue anchor.

3. The method according to inventive concept 1, wherein the proximal implant-penetrating element includes a post, and wherein advancing comprises advancing the implant until the implant reaches and is penetrated by the post.

4. The method according to inventive concept 3, further comprising restraining the implant from separating from the implant-penetrating element by coupling a proximal restraining element to the post within 2 mm of the proximal end of the post.

5. The method according to inventive concept 4, wherein restraining the implant comprises advancing a lock along the cord to between the implant and the proximal restraining element, the lock including (a) a distal portion configured to rest against the implant, and (b) an expandable proximal portion having a cross-sectional area at its resting state that is larger than a greatest cross-sectional area of the post and smaller than a greatest cross-sectional area of the proximal restraining element.

6. The method according to inventive concept 1, wherein the proximal implant-penetrating element includes a barb, and wherein the method further comprises restraining the implant from separating from the implant-penetrating element by penetrating the barb through the implant.

7. The method according to inventive concept 6, wherein the barb includes one or more arms that are radially expandable, and wherein the method further comprises:

passing the one or more arms through the implant in a compressed state thereof, and restraining the implant from separating from the implant-penetrating element by allowing the one or more arms to expand and rest against an outer surface of the implant following the penetrating of the barb through the implant.

8. The method according to inventive concept 6, wherein the proximal implant-penetrating element includes an elastic portion that is configured to assume a first length when relaxed, and a second, greater length when under load, and wherein penetrating the barb through the implant comprises pulling the barb through the implant by pulling on the cord.

9. The method according to inventive concept 8, wherein the elastic portion includes a tension spring.

10. The method according to inventive concept 3, wherein the proximal restraining element is coupled within 2 mm of the proximal end of the post, and wherein restraining the implant from separating from the implant-penetrating element comprises restraining the implant from separating from the implant-penetrating element by the proximal restraining element is coupled within 2 mm of the proximal end of the post.

11. The method according to inventive concept 3, further comprising restraining the implant from separating from the implant-penetrating element by a proximal restraining element that is coupled to a proximal end of the post.

12. The method according to inventive concept 11, wherein restraining the implant comprises advancing a lock along the cord to between the implant and the proximal restraining element, the lock including (a) a distal portion configured to rest against the implant, and (b) an expandable proximal portion having a cross-sectional area at its resting state that is larger than a greatest cross-sectional area of the post and smaller than a greatest cross-sectional area of the proximal restraining element.

13. The method according to inventive concept 11, wherein the proximal implant-penetrating element includes a barb, and wherein restraining the implant from separating from the implant-penetrating element comprises penetrating the barb through the implant.

14. The method according to inventive concept 13, wherein the barb includes one or more arms that are radially expandable, and wherein the method further comprises:
passing the one or more arms through the implant in a compressed state thereof, and
restraining the implant from separating from the implant-penetrating element by allowing the one or more arms to expand and rest against an outer surface of the implant following the penetrating of the barb through the implant.

15. The method according to inventive concept 13, wherein the proximal implant-penetrating element includes an elastic portion that is configured to assume a first length when relaxed, and a second, greater length when under load, and wherein penetrating the barb through the implant comprises pulling the barb through the implant by pulling on the cord.

16. The method according to inventive concept 15, wherein the elastic portion includes a tension spring.

17. The method according to inventive concept 1, wherein coupling comprises coupling the distal tissue coupling element to the tissue at a site within a heart chamber of the patient, and wherein the method further comprises, after the advancing of the implant over the cord:
cutting the cord at a site outside of the heart chamber; and
withdrawing the cord from the passage.

18. The method according to inventive concept 1, wherein coupling comprises coupling the distal tissue coupling element to the tissue at a site within a heart chamber of the patient, and wherein the method further comprises, after the advancing of the implant over the cord, withdrawing the cord from the passage.

19. The method according to inventive concept 1, wherein the implant includes an annuloplasty device, and wherein advancing the implant comprises advancing the device over the cord until the device reaches and is penetrated by the proximal implant-penetrating element.

20. The method according to inventive concept 19, wherein coupling the distal tissue coupling element and advancing the device comprise coupling and advancing during a transcatheter procedure.

21. The method according to inventive concept 19, wherein advancing the device comprises advancing the device into an atrium of a heart of the patient in a vicinity of an annulus of an atrioventricular valve.

22. The method according to inventive concept 19, further comprising tightening the annuloplasty device by winding a flexible contracting member of the device around a spool coupled to the device.

23. A method comprising:
coupling, to a first portion of cardiac tissue of a patient, a distal tissue coupling element of a tissue anchor, which tissue anchor further includes (a) a proximal implant-receiving element, and (b) a cord, which is removably coupled to the implant-receiving element;
passing the cord through a tissue-repair implant;
advancing the implant over the cord until the implant reaches and is received at least in part by the proximal implant-receiving element, the proximal implant-receiving element comprising a proximal implant-restraining element; and
restraining the implant from separating from the implant-receiving element by the proximal implant-restraining element.

24. The method according to inventive concept 23, wherein coupling the distal tissue coupling element comprises:
coupling a distal tissue coupling element that comprises one or more radially-expandable prongs configured to expand and facilitate anchoring of the coupling element, and
by the coupling, restricting proximal motion of the tissue anchor.

25. The method according to inventive concept 23, wherein the proximal implant-receiving element includes a post, wherein the proximal implant-restraining element is coupled to a proximal portion of the post, and wherein advancing comprises advancing the implant until the implant reaches and is penetrated by the post.

26. The method according to inventive concept 25, wherein the proximal restraining element is coupled within 2 mm of the proximal end of the post, and wherein restraining the implant from separating from the implant-penetrating element comprises restraining the implant from separating from the implant-penetrating element by the proximal restraining element is coupled within 2 mm of the proximal end of the post.

27. The method according to inventive concept 25, wherein restraining the implant comprises advancing a lock along the cord to between the implant and the proximal restraining element, the lock including (a) a distal portion configured to rest against the implant, and (b) an expandable proximal portion having a cross-sectional area at its resting state that is larger than a greatest cross-sectional area of the post and smaller than a greatest cross-sectional area of the proximal implant-restraining element.

28. The method according to inventive concept 23, wherein the proximal implant-restraining element includes a barb, and wherein the method further comprises restraining the implant from separating from the implant-receiving element by penetrating the barb through at least a portion of the implant.

29. The method according to inventive concept 28, wherein the barb includes one or more arms that are radially expandable, and wherein the method further comprises:
passing the one or more arms through the implant in a compressed state thereof, and
restraining the implant from separating from the implant-receiving element by allowing the one or more arms to expand and rest against an outer surface of the implant following the penetrating of the barb through the implant.

30. The method according to inventive concept 28, wherein the proximal implant-receiving element includes an elastic portion that is configured to assume a first length when relaxed, and a second, greater length when under load, and wherein penetrating the barb through the implant comprises pulling the barb through the implant by pulling on the cord.
31. The method according to inventive concept 30, wherein the elastic portion includes a tension spring.
32. The method according to inventive concept 23, wherein coupling comprises coupling the distal tissue coupling element to the tissue at a site within a heart chamber of the patient, and wherein the method further comprises, after the advancing of the implant over the cord:
   cutting the cord at a site outside of the heart chamber; and
   withdrawing the cord from the passage.
33. The method according to inventive concept 23, wherein coupling comprises coupling the distal tissue coupling element to the tissue at a site within a heart chamber of the patient, and wherein the method further comprises, after the advancing of the implant over the cord, withdrawing the cord from the tissue anchor.
34. The method according to inventive concept 23, wherein coupling the distal tissue coupling element and advancing the implant comprise coupling and advancing during a transcatheter procedure.
35. The method according to inventive concept 23, wherein advancing the implant comprises advancing the device into an atrium of a heart of the patient in a vicinity of an annulus of an atrioventricular valve.
36. The method according to inventive concept 23, further comprising adjusting a distance between the first portion of cardiac tissue and a second portion of cardiac tissue by winding a flexible contracting member of the device around a spool coupled to the implant.
37. The method according to inventive concept 23, wherein the implant includes an annuloplasty device, and wherein advancing the implant comprises advancing the device over the cord until the device reaches and is penetrated by the proximal implant-receiving element.
38. The method according to inventive concept 37, further comprising tightening the annuloplasty device by winding a flexible contracting member of the device around a spool coupled to the device.

The present invention will be more fully understood from the following detailed description of applications thereof, taken together with the drawings, in which:

BRIEF DESCRIPTION OF THE DRAWINGS

FIGS. 2A-C are schematic illustrations of the tissue anchor and a delivery tool therefor, in accordance with some applications of the present invention;

FIG. 4 is a schematic illustration of a valve-repair implant being advanced toward the plurality of anchors of FIG. 3, in accordance with some applications of the present invention;

FIGS. 5A-B, 6A-B, and 7 are schematic illustrations of respective locking mechanisms for each of the tissue anchors of FIGS. 3-4, in accordance with some applications of the present invention;

FIGS. 8 and 9 are schematic illustrations of examples of valve-repair implants which are received by the tissue anchors of FIGS. 3-4, in accordance with respective applications of the present invention;

FIG. 10 is a schematic illustration of a tissue anchor for receiving a valve-repair implant, in accordance with another application of the present invention;

FIGS. 12-14 are schematic illustrations of a manipulator for implanting the tissue anchors or FIGS. 2A-C and 10 during a minimally-invasive or open-heart procedure, in accordance with some applications of the present invention;

FIG. 19 is a schematic illustration of the tissue anchor of FIGS. 2A-C in accordance with some applications of the present invention; and FIG. 20 is a schematic illustration of the tissue anchor of FIG. 10, in accordance with some applications of the present invention.

DETAILED DESCRIPTION OF APPLICATIONS

Figure 1A:
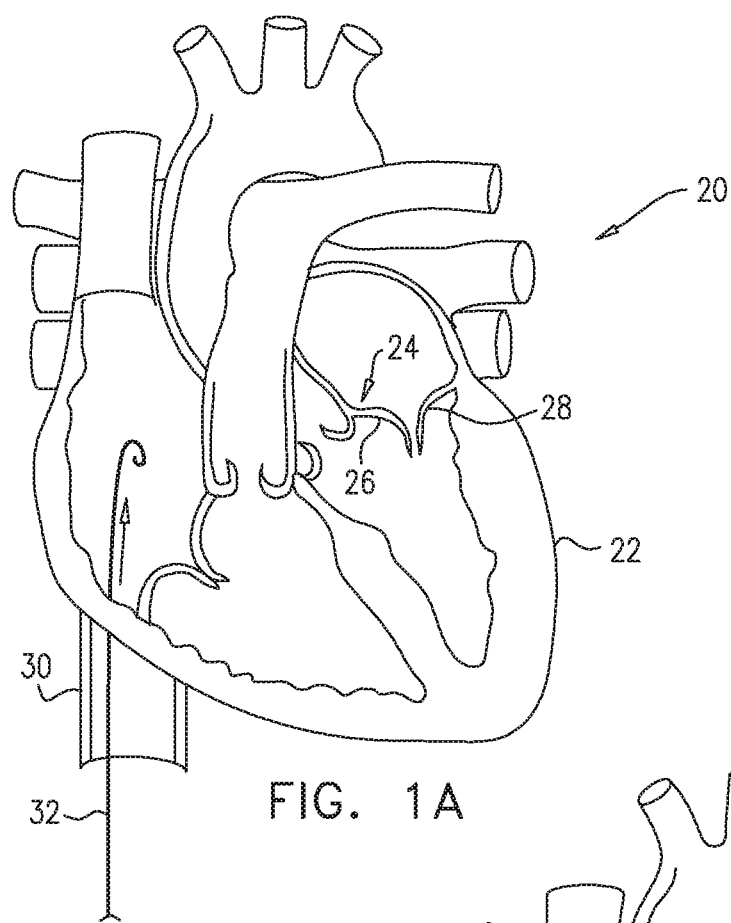
FIGS. 1A-F are schematic illustrations of a procedure for implanting a tissue anchor for receiving a valve-repair implant, in accordance with some applications of the present invention.

Reference is now made to FIGS. 1A-F, 2A-C, and 3, which are schematic illustrations of a system 20 for implanting a tissue anchor 49, in accordance with some applications of the present invention. FIGS. 1A-F show a transcatheter procedure for implanting tissue anchor 49. FIGS. 2A-C show a transcatheter delivery tool 42 for delivering toward and implanting anchor 49 at an implantation site, e.g., an annulus 25 of a heart 22 of a patient, as shown. Typically, the implantation site includes an annulus of an atrioventricular valve, e.g., a mitral valve or a tricuspid valve. It is to be noted that the implantation site is not limited to a heart valve of the patient, and anchor 49 may be implanted in other tissue of the patient, e.g., a portion of the inner wall of the heart of the patient, in a stomach of a patient, etc. Tissue anchor 49, as shown in FIG. 2B comprises a distal tissue coupling element 50, e.g., a helical tissue anchor 58, and a proximal implant-penetrating element 47a. Proximal implant-penetrating element 47a comprises a post 52a and a proximal implant-restraining element 53a which is configured to puncture and pass through a portion of a valve-repair implant, as will be described hereinbelow. Proximal restraining element 53a (i.e., a portion of implant-penetrating element 47a) is shaped so as to define a passage 56 therethrough. A cord 54 is removably coupled to anchor 49 by being passed through passage 56. Cord 54 functions to facilitate guiding of the valve-repair implant toward tissue anchor 49 implanted at annulus 25.

Reference is now made to FIGS. 1A-F, 2A-C, and 3-4 which are schematic illustrations of a procedure for implanting a plurality of tissue anchors 49 in order to repair a mitral valve 24 of the patient, in accordance with some applications of the present invention. Mitral valve 24 is shown including leaflets 26 and 28. The procedure is typically performed with the aid of imaging, such as fluoroscopy, transesophageal echo, and/or echocardiography.

The procedure typically begins by advancing a semi-rigid guidewire 32 into a right atrium of the patient, as shown in FIG. 1A.

Figure 1B:
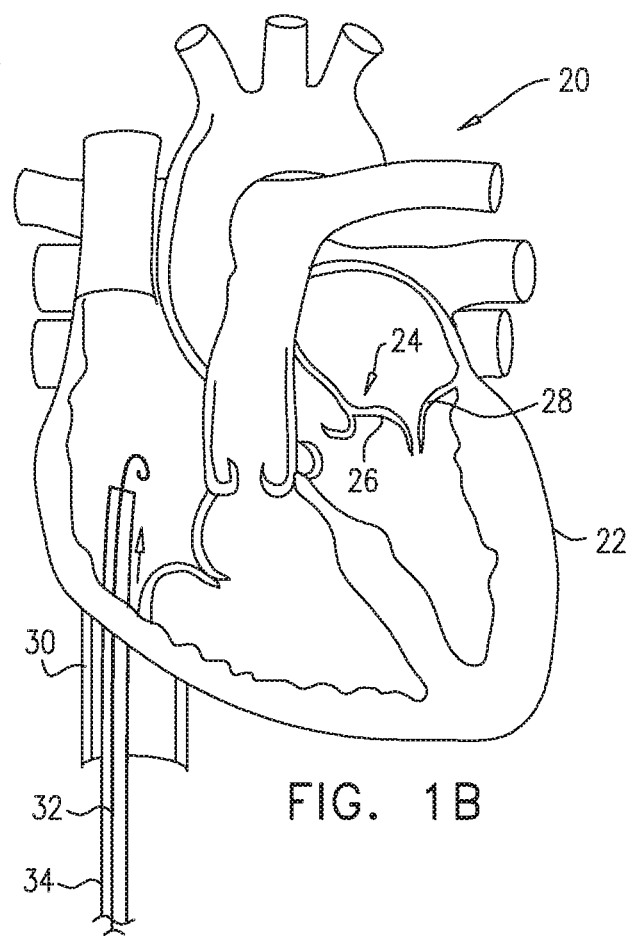

As show in FIG. 1B, guidewire 32 provides a guide for the subsequent advancement of a sheath 34 therealong and into the right atrium. Once sheath 34 has entered the right atrium, guidewire 32 is retracted from the patient's body. Sheath 34 typically comprises a 14-20 F sheath, although the size may be selected as appropriate for a given patient. Sheath 34 is advanced through vasculature into the right atrium using a suitable point of origin typically determined for a given patient. For example:

sheath 34 may be introduced into the femoral vein of the patient, through an inferior vena cava 30, into the right atrium, and into a left atrium transseptally, typically through the fossa ovalis;

sheath 34 may be introduced into the basilic vein, through the subclavian vein to the superior vena cava, into the right atrium, and into the left atrium transseptally, typically through the fossa ovalis; or sheath 34 may be introduced into the external jugular vein, through the subclavian vein to the superior vena cava, into the right atrium, and into the left atrium transseptally, typically through the fossa ovalis.

In some applications of the present invention, sheath 34 is advanced through an inferior vena cava 30 of the patient (as shown) and into the right atrium using a suitable point of origin typically determined for a given patient.

(In this context, in the specification and in the claims, "proximal" means closer to the orifice through which system 20 is originally placed into the body of the patient, and "distal" means further from this orifice.)

Figure 1C:
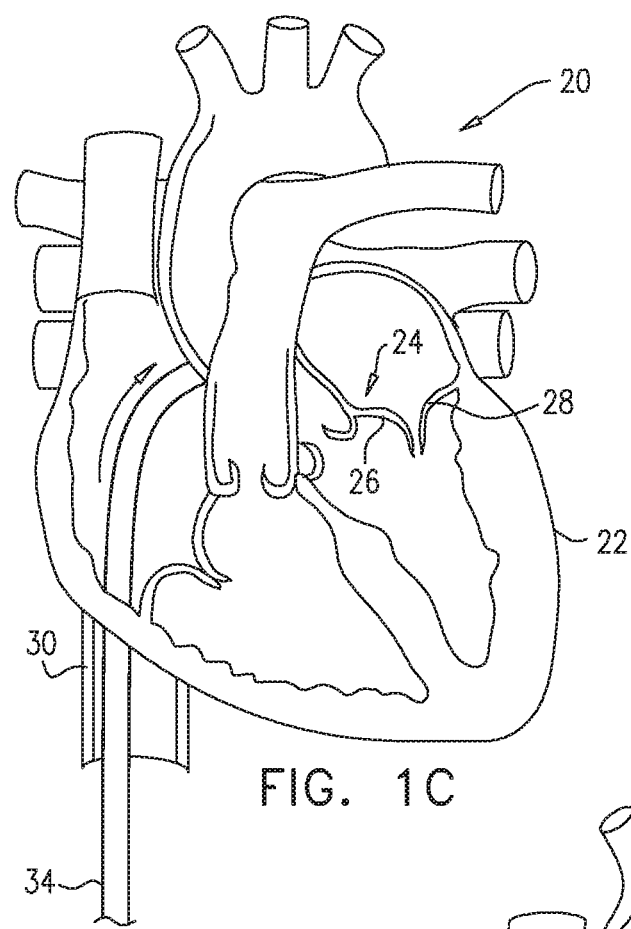

Sheath 34 is advanced distally until the sheath reaches the interatrial septum, as shown in FIG. 1C.

Figure 1D:
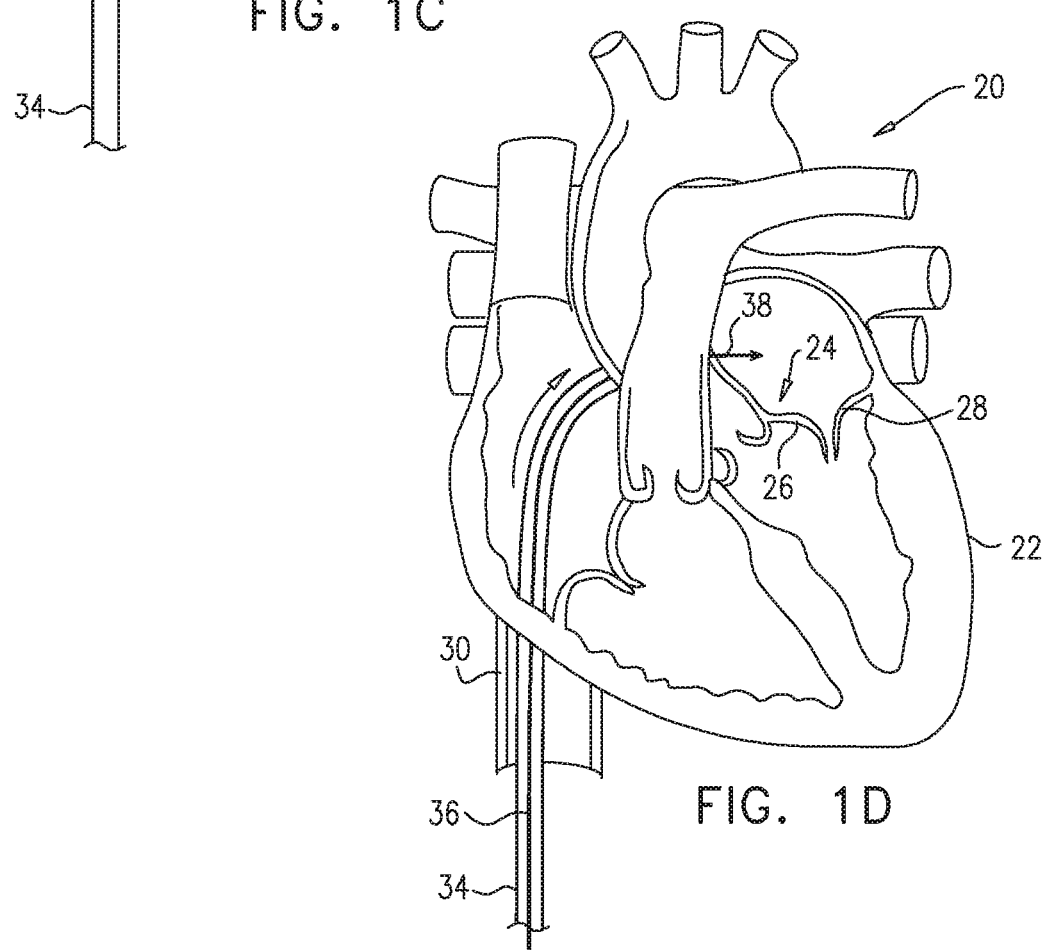

As shown in FIG. 1D, a resilient needle 38 coupled to an elongate wire 36 and a dilator (not shown) are advanced through sheath 34 and into heart 22. In order to advance sheath 34 transseptally into the left atrium, the dilator is advanced to the septum, and needle 38 is pushed from within the dilator and is allowed to puncture the septum to create an opening that facilitates passage of the dilator and subsequently sheath 34 therethrough and into the left atrium. The dilator is passed through the hole in the septum created by the needle. Typically, the dilator is shaped to define a hollow tube shaft for passage along needle 38, and the hollow tube shaft is shaped to define a tapered distal end. This tapered distal end is first advanced through the hole created by needle 38. The hole is enlarged when the gradually increasing diameter of the distal end of the dilator is pushed through the hole in the septum.

Figure 1E:
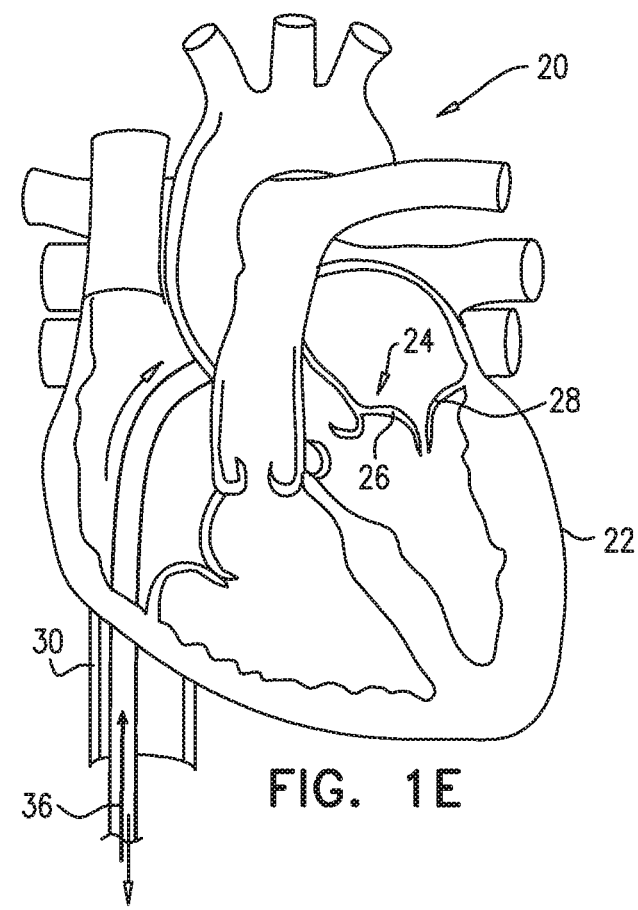

The advancement of sheath 34 through the septum and into the left atrium is followed by the extraction of the dilator and needle 38 from within sheath 34, as shown in FIG. 1E.

Figure 1F:
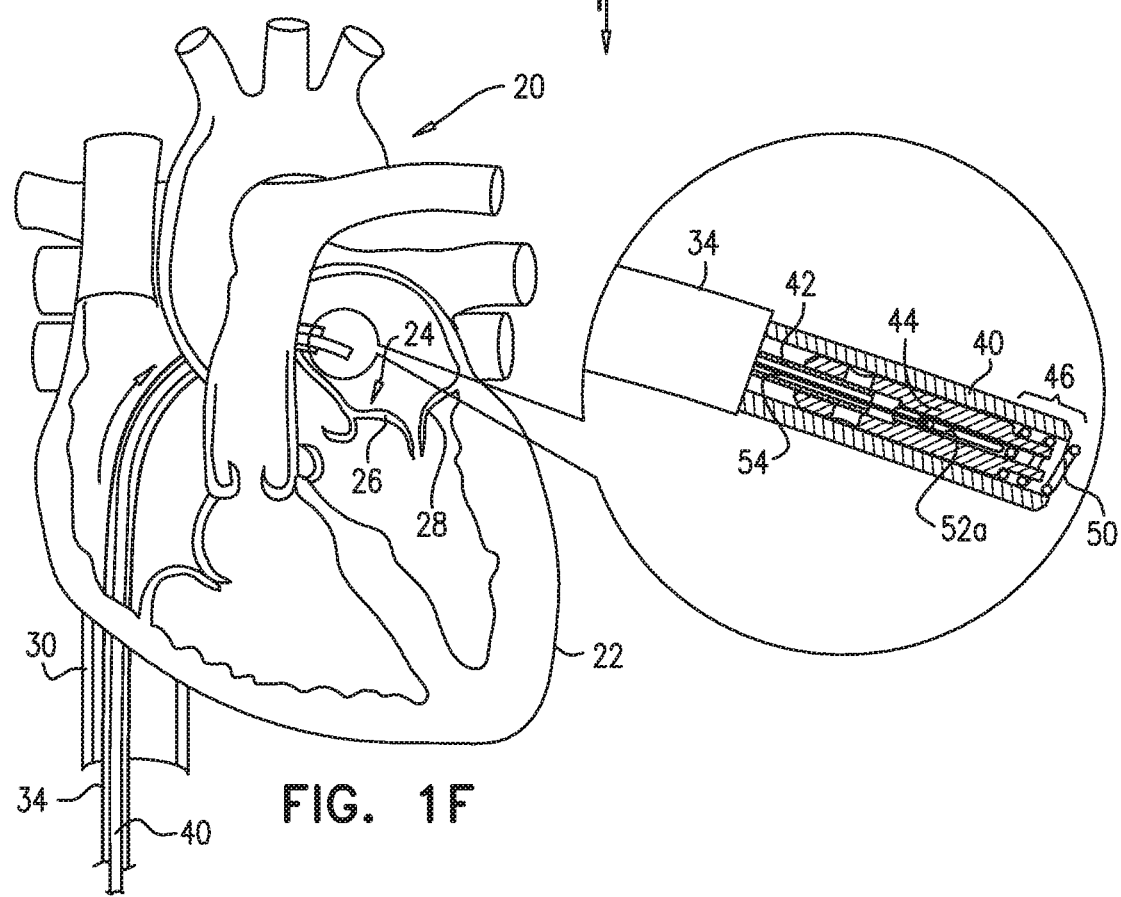

Subsequently, as shown in FIG. 1F, delivery tool 42 is advanced within an advancement catheter 40 and through sheath 34. Delivery tool 42 comprises an elongate tube shaft that is coupled at a distal end thereof to a manipulator 44. Manipulator 44 reversibly engages anchor 49 and facilitates the delivery of anchor 49 to the left atrium and the subsequent implantation of anchor 49 in tissue of annulus 25 of the patient. Delivery tool 42 is described hereinbelow with reference to FIGS. 2A-C.

FIG. 2A shows delivery tool 42 disposed within advancement catheter 40, which slides through sheath 34 and toward annulus 25 of heart 22. Delivery tool 42, manipulator 44, and anchor 49 are shown in cross-section.

FIG. 2B shows the relative spatial configurations of delivery tool 42, manipulator 44, and anchor 49. Anchor 49 comprises a distal tissue coupling element 50 having a pointed distal tip 51 configured for puncturing tissue of the patient. Distal tissue coupling element 50 comprises a helical tissue anchor 58, by way of illustration and not limitation, e.g., tissue coupling element 50 may comprise any suitable tissue anchor known in the art (e.g., as is shown hereinbelow in FIGS. 19 and 20). For example, distal tissue coupling element 50 may comprise any suitable tissue anchor known in the art (e.g., a spiral or a screw shaft) or any tissue anchor as described in PCT Patent Application PCT/IL2009/000593 to Gross et al., entitled, "Annuloplasty devices and methods of delivery therefor," filed Jun. 15, 2009, which published as WO 10/004546, and which is incorporated herein by reference.

Reference is now made to FIGS. 2A-B. The helical coils of helical tissue anchor 58 form a generally-cylindrical coil surrounding a lumen of helical tissue anchor 58. Helical tissue anchor 58 is shaped to provide a bar 55 which projects into the lumen of helical tissue anchor 58. A distal portion 57 of implant-penetrating element 47a is coupled, e.g., welded, to bar 55.

Reference is again made to FIG. 2B. Anchor 49, comprising distal tissue coupling element 50 and implant-penetrating element 47a, has a length L1 of 6-18, e.g., 6-12 mm, e.g., 10 mm. In some applications of the present invention, distal tissue coupling element 50 and implant-penetrating element 47a are separate pieces that are coupled, e.g., welded, to one another. Alternatively, distal tissue coupling element 50 and implant-penetrating element 47a are fabricated from a single piece. Implant-penetrating element 47a has a length L2 of 4-10 mm, e.g., 5.5 mm. Distal tissue coupling element 50 has a length L3 of 2-8 mm, e.g., 4 mm. Implant-penetrating element 47a comprises a post 52a and proximal restraining element 53a. Post 52a has a length of between 1 and 7 mm, e.g., 5.5 mm and a greatest cross-sectional area (measured at a plane that is perpendicular to the axis along which the length of post 52a is measured) of between 0.03 and 0.2 mm^2, e.g., 0.13 mm^2, which length is at least 4 times (e.g., 5, 8, or 10 times) the square root of the greatest cross-sectional area. Post 52a has a longest dimension at its cross-section of between 0.2 mm and 0.5 mm (e.g., 0.4 mm). That is, for example, post 52a has a length of 5.5 mm and a longest cross-sectional dimension (measured at the plane that is perpendicular to the axis along with the length of post 52a is measured) of 0.4 mm. In such an example, the ratio of the length to the longest cross-sectional dimension is around 13.75:1. For some applications, this ratio is between 5:1 and 14:1, and the ratio varies depending on the size of the implant that is anchored to the tissue of the patient via anchor 49.

It is to be noted that anchors 49 may be used to implant any implant of any suitable size to any tissue of the patient, and that the ratio of length to the longest cross-sectional dimension of post 52a of between 5:1 and 14:1 varies depending on the size of the implant that is anchored to the patient.

Proximal restraining element 53a, is coupleable or coupled to post 52a within 2 mm of the proximal end of post 52a. For some applications, as recited above, implant-penetrating element 47a comprises proximal restraining element 53a. Proximal restraining element 53a has a longest dimension at its cross-section (measured at a plane that is perpendicular to the axis along which the length L1 is measured) of between 0.3 mm and 0.75 mm, e.g., 0.6 mm. Proximal restraining element 53a has a greatest cross-sectional area of between 0.07 and 0.44 mm^2, (e.g., 0.28 mm^2) that is at least 1.5 times a greatest cross-sectional area of post 52a. Following the subsequent implantation of the valve-repair implant, as will be described hereinbelow, proximal restraining element 53a restrains the implant from sliding proximally along post 52a and separating from implant-penetrating element 47a. Implant-penetrating element 47a is thus shaped to provide an elongate penetration having a sufficient length-to-width ratio for penetrating the implant and for passing through the lumen of the implant such that proximal restraining element 53a is disposed proximally to the outer surface of the implant. In this configuration, proximal restraining element 53a restrains the implant from separating from implant-penetrating element 47a, as is described hereinbelow.

Proximal restraining element 53a is shaped so as to define a passage 56 therethrough, which passage has at least two openings that are within 1 mm, e.g., such as 0.5 mm, of a proximal end of implant-penetrating element 47a. Cord 54 is looped through passage 56 and is thereby removably coupled to anchor 49. As shown in FIG. 2C, the two portions of cord 54 that project away from passage 56 of proximal restraining element 53a, are joined, e.g., welded, together at site proximal to tissue anchor 49, e.g., at a site outside the body of the patient, in order to form a single proximal end portion 59 of cord 54. End portion 59 of cord 54 is ultimately threaded through the implant outside the body of the patient in order for the implant to be slid along cord 54 and toward tissue anchor 49 at annulus 25. Once the implant is implanted at the annulus of the patient, cord 54 is cut distally to single proximal end portion 59 so as to sever the loop created by the joining of the two portions of cord 54 at end portion 59. Once cord 54 is cut, the physician extracts cord 54 from within the body of the patient as he or she pulls on proximal end portion 59 until cord 54 is pulled from within passage 56 of proximal restraining element 53a and is decoupled from anchor 49.

Reference is again made to FIG. 2A. As shown in the cross-sectional illustration, delivery tool 42 and manipulator 44 are each shaped so as to define a central lumen for cord 54 that is coupled to proximal restraining element 53a of implant-penetrating element 47a. Cord 54 comprises a wire, a ribbon, a rope, or a band, which typically comprises a flexible and/or superelastic material, e.g., nitinol, ePTFE, PTFE, polyester, stainless steel, or cobalt chrome. In some applications of the present invention, cord 54 comprises a braided polyester suture (e.g., Ticron). In some applications of the present invention, cord 54 is coated with polytetrafluoroethylene (PTFE). In some applications of the present invention, cord 54 comprises a plurality of wires that are intertwined to form a rope structure.

Manipulator 44 is disposed at the distal end of the tube shaft of delivery tool 42 and is shaped to provide a distal applicator portion 46 which has a smaller outer diameter than an outer diameter of a proximal portion of manipulator 44. As shown in the cross-sectional illustration of manipulator 44 and anchor 49 in FIG. 2A, distal applicator portion 46 is shaped so as to fit within a lumen of distal tissue coupling element 50 (i.e., the outer diameter of portion 46 is smaller than an inner diameter of distal tissue coupling element 50). Manipulator 44 is shaped so as to define a slit 48 which bisects the distal end portion of manipulator 44 into two lateral walled portions. Slit 48 functions as a housing for housing and reversibly coupling implant-penetrating element 47a to delivery tool 42 (as shown in FIG. 2A). Slit 48 holds in place anchor 49 as it is advanced toward annulus 25. Delivery tool 42 then functions to implant distal tissue coupling element 50 of anchor 49 in tissue of annulus 25. First, torque is delivered toward manipulator 44 in response to rotation of the tube shaft of delivery tool 42. Responsively to the torque, the lateral walled portions at the distal portion of manipulator 44 and distal applicator portion 46 function as a screw-driving tool by applying annular force to implant-penetrating element 47a and helical tissue anchor 58.

As shown in FIG. 2A, bar 55 of distal tissue coupling element 50 functions to couple anchor 49 to manipulator 44 when bar 55 is received and disposed within slit 48 and surrounded by the lateral wall portions of manipulator 44.

Figure 3:
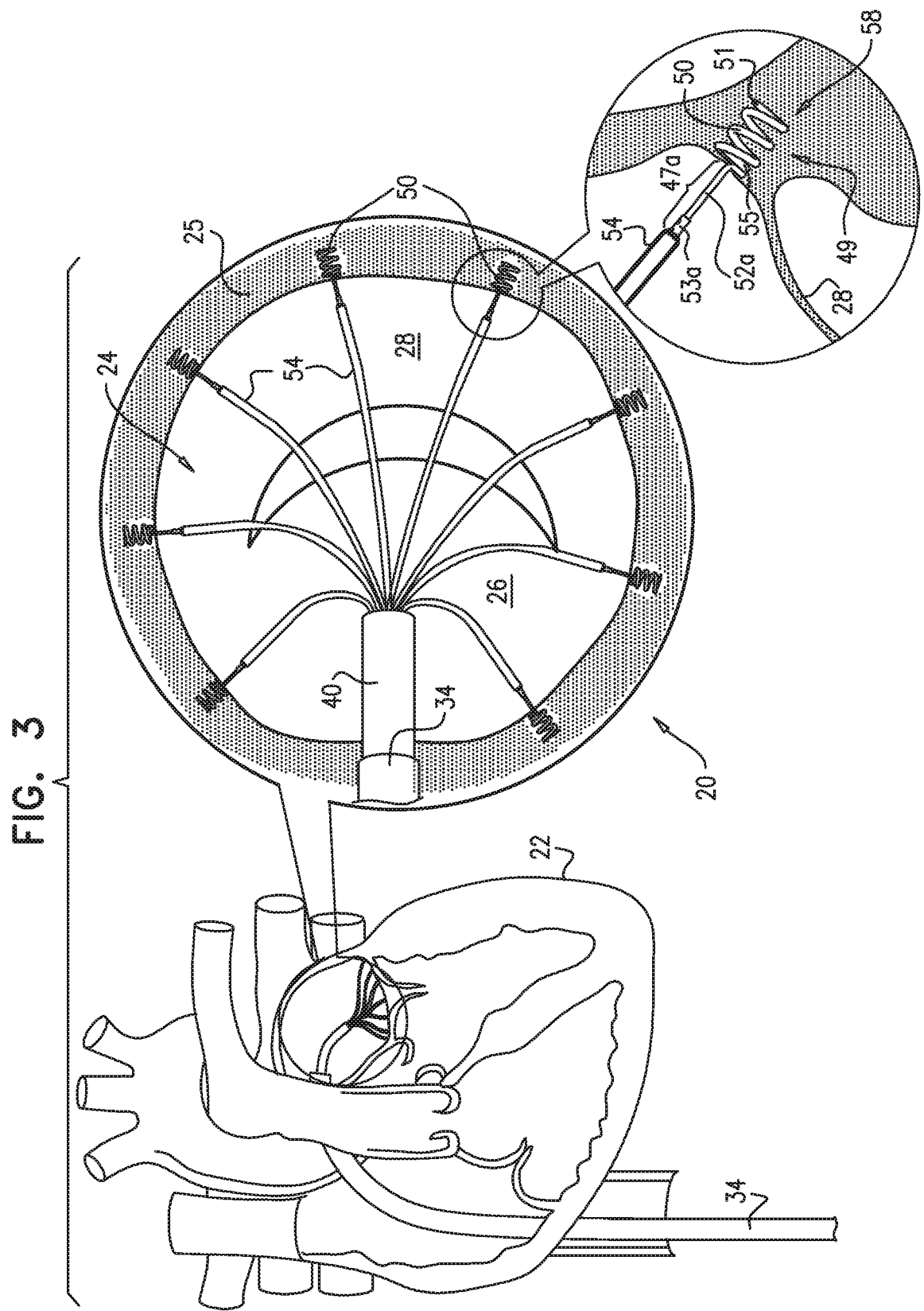
FIG. 3 is a schematic illustration of a plurality of the tissue anchors of FIGS. 2A-C implanted along an annulus of a patient, in accordance with some applications of the present invention.

FIG. 3 shows a plurality of anchors 49 implanted in respective portions of tissue of annulus 25 around a perimeter thereof. Each anchor 49 is implanted such that a central longitudinal axis therethrough forms an angle of between about 45 and 90 degrees with a surface of the tissue of annulus 25, such as between about 75 and 90 degrees, e.g., about 90 degrees. The physician uses delivery tool 42, as described hereinabove to systematically advance each anchor 49 through sheath 34 and toward annulus 25. A first anchor 49 is coupled to manipulator 44 of delivery tool 42, as follows: (a) cord 45 is fed through the lumen of the tube shaft of delivery tool 42 and through the lumen of manipulator 44, and (b) distal applicator portion 46 of manipulator 44 is advanced within the lumen of helical tissue anchor 58, while (c) bar 55 of helical tissue anchor 58 is advanced in place within slit 48 of manipulator 44. The relative spatial configurations anchor 49 and manipulator 44 when anchor 49 is coupled to manipulator 44 is shown hereinabove with reference to FIG. 2A.

Delivery tool 42 is then fed within advancement catheter 40, and catheter 40 is advanced within sheath 34 toward annulus 25 until a distal end of catheter 40 emerges from within the distal end of sheath 34 and into the left atrium of the patient. Advancement catheter 40 is advanced toward a given location along annulus 25. Subsequently, the tube shaft of delivery tool 42 is pushed such that distal tip 51 of helical tissue anchor 58 abuts the surface of tissue of the annulus. Torque is then delivered to manipulator 44 when the physician rotates the tube shaft of delivery tool 42 about a central axis of tool 42. Such rotation of tool 42 rotates manipulator 44 in a manner in which the distal walled portions of the distal end of manipulator 44 apply an annular force to helical tissue anchor 58. Responsively to the continued application of the annular force to helical tissue anchor 58, distal tip 51 punctures the tissue of annulus 25 and continues along a helical path until helical tissue anchor 58 is corkscrewed sufficiently into tissue of annulus 25 at the given location. For applications in which distal tissue coupling element 50 comprises any other tissue coupling anchor, delivery tool 42 or any other delivery tool facilitates coupling of anchor 49 to annulus 25 by advancing distal tissue coupling element 50 into the tissue of annulus 25.

Following the corkscrewing of helical tissue anchor 58 into tissue of the annulus, the physician pulls slightly on the tube shaft of delivery tool 42. Upon applying the pulling force to tool 42, the tissue of the annulus responsively pulls on the corkscrewed distal tissue coupling element 50, thereby pulling implant-penetrating element 47a from within slit 48 of manipulator 44 and disengaging anchor 49 from tool 42. As implant-penetrating element 47a is pulled from and slides distally within slit 48, it frees anchor 49 from manipulator 44. Delivery tool 42, freed from anchor 49, is then retracted within catheter 40, and catheter 40 is extracted from within the body through sheath 34 which remains in place for the subsequent advancements of the remaining anchors 49. As delivery tool 42 and catheter 40 are extracted, cord 45 remains looped within passage 56 of proximal restraining element 53a and is left disposed within sheath 34 such that proximal end portion 59 of cord 54 is disposed and accessible outside the body of the patient.

Once outside the body of the patient, delivery tool 42 is then coupled to a second anchor 49 (as described hereinabove with reference to the coupling of anchor 49 to manipulator 44), and tool 42 is fed into advancement catheter 40 which is then reintroduced into sheath 34. The second anchor 49 is implanted, as described hereinabove. These steps are repeated until all of the anchors have been implanted around annulus 25, as shown in FIG. 3. As shown, cords 45 reversibly coupled to each anchor 49 are disposed within sheath 34 and are accessible at their respective proximal portions 59 at a site outside the body of the patient. It is to be noted that although eight anchors 49 are implanted around annulus 25 by way of illustration and not limitation, any suitable number of anchors 49 may be implanted along annulus 25 according to the needs of a given patient, e.g., depending on the level of distention and relaxation of the annulus of a given patient.

Reference is now made to FIG. 4, which is a schematic illustration of a tissue-repair implant 60 being advanced along cords 54 toward annulus 25 of the mitral valve of the patient. As shown, repair implant 60 comprises a noncontinuous, open, partial annuloplasty ring 300, by way of illustration and not limitation. It is to be noted that any valve-repair device, or implant (e.g., a full annuloplasty ring, a partial annuloplasty ring, a prosthetic valve, or a docking station for a prosthetic valve such as an annular valve support member) may be advanceable along cords 54. The partial, open ring of repair implant 60 may be implemented using any one of the techniques described in U.S. patent application Ser. No. 12/341,960 to Cabiri, which issued as U.S. Pat. No. 8,241,351, and which is incorporated herein by reference. Typically, these techniques describe a full or partial ring comprising a sleeve, a spool 302 coupled to the sleeve 304, and a flexible contracting member 306 that is coupled to the spool 302 and the sleeve 304, such that (1) winding the contracting member 306 around the spool 302 tightens the ring 300, and (2) unwinding the contracting member 306 from around the spool 302 relaxes and expands the ring 300. As shown, implant 60 comprises a penetrable sleeve 304 comprising a braided fabric mesh. Implant 60 may also comprise a coiled implant in addition to or independently of the sleeve 304.

Reference is made to FIGS. 2C and 4. Prior to the advancing of implant 60, a respective proximal end portion 59 of each cord 54 is threaded through the material of repair implant 60. For example, end portion 59 is threaded (a) through a first surface of implant 60, (b) through the lumen of implant 60 such that portion 59 passes orthogonal to the longitudinal axis defined by the lumen of implant 60, and then (c) through an opposing surface of implant 60 such that it emerges proximal to the outer surface of implant 60. A pushing tool (not shown for clarity of illustration) is used to advance implant 60 through advancement catheter 40 (which is advanced through sheath 34) and along each cord 54 toward annulus 25. Once implant 60 emerges from within catheter 40, the pushing tool is retracted and extracted from the body. Subsequently, implant 60 is locked in place along annulus 25 via anchors 49, as is described hereinbelow.

FIGS. 5A-B show a locking mechanism 74 that comprises a lock 80 having an annular distal portion 82 that is coupled to a plurality of radially-collapsible prongs 84, in accordance with some applications of the present invention. Annular distal portion 82 has a diameter of between 1.5 mm and 3 mm, e.g., 2.2 mm. Following the advancement of mechanism 74 through the vasculature of the patient, lock 80 is ultimately positioned at a proximal portion of post 52a of implant-penetrating element 47a at a site distal to implant-restraining element 53a (FIG. 5B), as described hereinbelow.

It is to be noted that lock 80 also functions as a proximal restraining element to restrain implant 60 from sliding proximally away from anchor 49 and annulus 25.

Locking mechanism 74 is coupled to a distal end of an advancement tube 72 and is advanced toward annulus 25 of the patient while surrounded by an overtube 70. Locking mechanism 74 comprises a lock holder 73 which has radially-expandable arms 75 and 77. Each of arms 75 and 77 is shaped to define a respective slot 81 and 83 which each cup and receive respective portions of annular distal portion 82 of lock 80, as shown in the enlarged image of FIG. 5A. A distal portion of overtube 70 surrounds arms 75 and 77 during the advancement of locking mechanism 74 toward annulus 25 of the patient. Overtube 70 thus prevents arms 75 and 77 from radially expanding, and this maintains coupling between holder 73 and lock 80. As shown, locking mechanism 74, advancement tube 72, and overtube 70 are advanced toward implant 60, along cord 54.

The distal ends of advancement tube 72 and overtube 70 are advanced until they contact a proximal surface of a portion of implant 60. In response to continued pushing of tubes 70 and 72, tubes 70 and 72 push the portion of implant 60 distally such that implant 60 is penetrated by implant-penetrating element 47a (i.e., first by proximal restraining element 53a and then by post 52a). For some applications, proximal restraining element 53a is shaped to define a pointed tip, e.g., a barb, configure to puncture and penetrate a portion of implant 60. Once implant 60 is fully pushed, a distal surface of implant 60 contacts tissue of annulus 25 and the proximal surface of implant 60 is disposed distally to a distal end of proximal restraining element 53a. Post 52a couples implant 60 to anchor 49 by extending through a lumen of implant 60.

It is to be noted that implant-penetrating element 47a may penetrate the implant by penetrating a braided mesh surrounding the implant, may penetrate the implant by passing between coils of a coiled implant, and/or may penetrate the implant in any other penetrating manner.

FIG. 5B shows the disengaging of lock 80 from mechanism 74 following the locking in place of implant 60 to anchor 49 via lock 80. As described hereinbelow, once lock 80 is coupled to anchor 49, overtube 70 is slid proximally with respect to advancement tube 72 such that arms 75 and 77 of lock holder 73 are exposed from within the distal portion of overtube 70. Once arms 75 and 77 are exposed, they expand radially (as is their natural tendency), and respective portions of annular distal portion 82 of lock 80 are freed from within slots 81 and 83 of arms 75 and 77, respectively. Once lock 80 is freed from locking mechanism 74, advancement tube 72, locking mechanism 74, and overtube 70 are retracted from within the body of the patient. In conjunction with the retracting, cord 54 is clipped and pulled such that it is no longer looped within passage 56 of proximal restraining element 53a. The physician continues to pull cord 54 until cord 54 is extracted from within the body of the patient.

FIGS. 6A-B and 7 show the method for locking repair implant 60 to annulus 25 via anchor 49, in accordance with some applications of the present invention. As shown, post 52a of anchor 49 extends through the lumen of implant 60 from a distal surface of implant 60 (i.e., the surface in contact with annulus 25) to an opposing surface at the proximal surface of implant 60 (i.e., the surface in communication with the atrium of the patient). Post 52a extends through the lumen of implant 60 in a manner in which a distal end of proximal restraining element 53a is disposed proximally to the proximal surface of implant 60.

Overtube 70 (and advancement tube 72, locking mechanism 74, and lock 80 disposed in overtube 70) is advanced along cord 54 and toward anchor 49 implanted at a given location along annulus 25. The distal end of overtube 70 approaches the proximal surface of repair implant 60. Overtube 70 and advancement tube 72 are pushed so that locking mechanism 74 and lock 80 engage implant-penetrating element 47a of anchor 49. As tubes 70 and 72 are pushed, locking mechanism 74 is pushed toward implant 60, and mechanism 74 in turn, pushes on annular distal portion 82 of lock 80 in order to slide lock 80 distally and around proximal restraining element 53a. As annular distal portion 82 is pushed, prongs 84 slide along proximal restraining element 53a (FIG. 6A).

Typically, in their resting state, the proximal portions of prongs 84 are aligned in a manner in which they form a circle at their cross-section having a longest dimension measured at a cross-section (measured at a plane that is perpendicular to the longitudinal axis along which length L1 of implant 60 is measured) of between 0.25 mm and 0.6 mm, (e.g., 0.45 mm) and a greatest cross-sectional area of between 0.05 mm^2 and 0.28 mm^2, e.g., 0.16 mm^2. It is to be noted that the proximal portions of prongs 84 are aligned in a manner in which they form a circle by way of illustration and not limitation, and that proximal portions of prongs 84 may be shaped so as to assume any given shape at their cross-section having a greatest cross-sectional area during the resting state of between 0.05 mm^2 and 0.28 mm^2, e.g., 0.16 mm^2. Since proximal restraining element 53a has a longest dimension at its cross-section of between 0.3 mm and 0.75 mm, as prongs 84 are advanced distally over proximal restraining element 53a proximal restraining element 53a pushes the proximal portions of prongs 84 radially such that the proximal portions of prongs 84 expand from their resting state to assume a greatest cross-sectional area of between 0.33 and 0.64 mm^2, i.e., a longest dimension at the cross-section of between 0.65 mm and 0.9 mm. As the proximal portions of prongs 84 are radially pushed, their collective cross-sectional area is larger than the greatest cross-sectional area of proximal restraining element 53a.

In response to continued pushing of lock 80 by locking mechanism 74, lock 80 slides distally until the respective proximal ends of each prong 84 are disposed distally to the distal end of proximal restraining element 53a (shown in FIG. 6B). Since the greatest cross-sectional area of post 52a (i.e., between 0.03 mm^2 and 0.2 mm^2) is smaller than the greatest cross-sectional area of proximal restraining element 53a (i.e., between 0.07 mm^2 and 0.44 mm^2), the proximal portions of prongs 84 radially collapse around post 52a to assume a greatest cross-sectional area that is smaller than the greatest cross-sectional area of proximal restraining element 53a. Since the greatest cross-sectional area of proximal restraining element 53a is larger than the greatest collective cross-sectional area of the proximal portions of prongs 84 in their resting state and as they surround post 52a, prongs 84 are restricted from moving proximally because they have collapsed around post 52a. That is, when lock 80 moves proximally along post 52a, the proximal end portions of prongs 84 abut against the distal end of proximal restraining element 53a. In such a manner, proximal restraining element 53a, restrains prongs 84 of lock 80 from sliding proximally, and thereby proximal restraining element 53a, together with lock 80, restrain implant 60 from sliding proximally away from anchor 49 and from annulus 25. In such a manner, post 52a functions as a protrusion which protrudes into a plane defined by implant 60, and the distal portion of proximal restraining element 53a functions as a shelf which facilitates restricting of proximal portion of the implant along the protrusion. As described herein above with reference to the cross-sectional area of proximal restraining element 53a (measured at a plane that is perpendicular to the longitudinal axis along which length L1 of implant 60 is measured), the shelf has a transverse cross-sectional length (i.e., the cross-sectional area, as described hereinabove), that is larger than a transverse cross-sectional length of implant-penetrating element 47a.

Additionally, as lock 80 is pushed distally, annular distal portion 82 pushes against a portion of implant 60. Responsively, implant 60 pushes against annular distal portion 82 so as to (1) create pressure between the proximal portions of prongs 84 and the distal end of proximal restraining element 53a, and (2) lock lock 80 in place with respect to proximal restraining element 53a in order to restrain implant 60 from sliding proximally.

FIG. 7 shows the decoupling of lock holder 73 from lock 80 and from anchor 49. Overtube 70 is retracted proximally in order to expose arms 75 and 77 of lock holder 73. Once arms 75 and 77 are exposed from within overtube 70, they expand radially, as shown, and respective portions of annular distal portion 82 of lock 80 are freed from within slots 81 and 83 of arms 75 and 77, respectively. Overtube 70, advancement tube 72, and lock holder 73 are then retracted through sheath 34 along cord 54.

Reference is now made to FIGS. 2C and 7. Once lock 80 is locked in place between implant 60 and proximal restraining element 53a of anchor 49, cord 54 is clipped distally to proximal end portion 59 thereof so as to create free ends of cord 54. A first free end of cord 54 is then pulled so that the second free end is pulled through advancement tube 72 and toward anchor 49. In response to continued pulling of the first free end of cord 54, the second end of cord 54 is pulled through passage 56 of proximal restraining element 53a until cord 54 is decoupled from anchor 49. The physician continues to pull on the first free end of cord 54 until the second free end is once again exposed from within tube 72, and thereby cord 54 is extracted from within the body of the patient.

FIG. 7 shows the decoupling of lock holder 73 of locking mechanism 74 from one of the eight anchors 49 around annulus 25. It is to be noted that the method for the locking in place of implant 60 via anchors 49 and locks 80 (as described hereinabove with reference to FIGS. 5A-B, 6A-B, and 7) is applied to every anchor 49 implanted along annulus 25. FIG. 7 shows implant 60 comprising a partial, open, non-continuous ring as described in U.S. patent application Ser. No. 12/341,960 to Cabiri (which is incorporated herein by reference), by way of illustration and not limitation. For example, any suitable tissue repair device known in the art may be anchored to any tissue of the patient via anchor(s) 49. For example, anchors 49 may be implanted in a stomach of the patient and may be used to anchor a gastric bypass ring to the stomach of the patient, in a manner as described hereinabove.

FIGS. 8 and 9 are schematic illustrations of examples of the types of implants 60 that are anchored to annulus 25 via anchors 49, in accordance with respective applications of the present invention. FIG. 8 shows implant 60 comprising a partial, open, non-continuous annuloplasty ring by way of illustration and not limitation. FIG. 9 shows a system 110 in which implant 60 comprises a full annuloplasty ring by way of illustration and not limitation. As described hereinabove implants 60, as shown in FIGS. 8 and 9, are shown by way of illustration and not limitation and that any suitable tissue-remodeling device or implant may be anchored to tissue of the patient using anchor(s) 49.

Reference is now made to FIG. 10, which is a schematic illustration of a system 120 comprising a tissue anchor 121 comprising a distal tissue coupling element 50 and a proximal implant-penetrating element 47b, in accordance with some applications of the present invention. Implant-penetrating element 47b comprises a proximal elastic portion comprising a tension spring 122 and a proximal restraining element 53b comprising radially-expandable anchor arms 128. Implant-penetrating element 47b comprises a proximal portion 124 shaped to define a pointed tip 126 for penetrating an implant (e.g., a tissue-repair implant 60) and facilitating passage of the implant over implant-penetrating element 47b. Typically, proximal portion 124, pointed tip 126, and arms 128 together form and function as a barb 153. A proximal elastic portion comprises a tension spring 122 (i.e., implant-penetrating element 47b), as shown by way of illustration and not limitation, and has a length L4 of between 3 mm and 5 mm, e.g., 4 mm, when spring 122 is relaxed. Radially-expandable arms 128 are compressible and expandable along a longitudinal axis 130 of anchor 121. Distal tissue coupling element 50 comprises a distal tissue-penetrating tip 51 and is shaped to define helical tissue anchor 58 by way of illustration and not limitation, e.g., tissue coupling element 50 may comprise any suitable tissue anchor known in the art (e.g., as is shown hereinbelow in FIGS. 19 and 20).

It is to be noted that proximal implant-penetrating element 47b of anchor 121 is similar in function to proximal implant-penetrating element 47a of anchor 49 in that both proximal implant-penetrating elements 47a and 47b function to receive and facilitate coupling of the implant to the tissue anchor. It is to be further noted that proximal restraining element 53b of anchor 121 is similar in function to proximal restraining element 53a of anchor 49 in that both proximal restraining elements 53a and 53b function to restrain the implant from sliding proximally and separating from respective implant-penetrating elements 47a and 47b.

As described hereinabove, distal tissue coupling element 50 has length L3 of 2-8 mm, e.g., 4 mm. Thus, for some applications, anchor 121 has a total length L5 of 5-13 mm.

The elastic portion is shown in FIG. 10 when spring 122 is in its relaxed, resting state. In this relaxed state of spring 122, the elastic portion has a length of between 3 and 5 mm. Spring 122 is configured to be pulled during one stage of implantation of the tissue-repair device. During such pulling, spring 122 is under load and assumes a greater length when under load than when in its relaxed state.

The proximal portion of implant-penetrating element 47b is shaped so as to define one or more passages 56 therethrough. It is to be noted that only one opening of one passage 56 is shown in the configuration as shown in FIG. 10, and that cord 54 passes through passage 56 on the sides of proximal portion 124. Cord 54 is removably coupled to anchor 121 by being passed through passage 56 (as described hereinabove with reference to anchor 49) and functions to facilitate guiding of the valve-repair implant toward tissue anchor 121 implanted at annulus 25. As described hereinabove, passage 56 has at least two openings that are within 1 mm, e.g., 0.5 mm, of a proximal end of implant-penetrating element 47b.

The distal portion of implant-penetrating element 47b comprises a post 52b which couples distal tissue coupling element 50 to the elastic portion. Post 52b in such an application has a height of between 0.2 mm and 0.4 mm. Anchor 121, comprising distal tissue coupling element 50 and implant-penetrating element 47b, has a length measured along axis 130 of 6-12 mm, e.g., 10 mm. Implant-penetrating element 47b has a length measured along axis 130 of 4-10 mm, e.g., 5.5 mm. Distal tissue coupling element 50 has a length measured along axis 130 of 2-8 mm, e.g., 4 mm. For some applications, post 52b includes spring 122, and in such an application, post 52b has a length of between 1 and 7 mm.

Figure 11A:
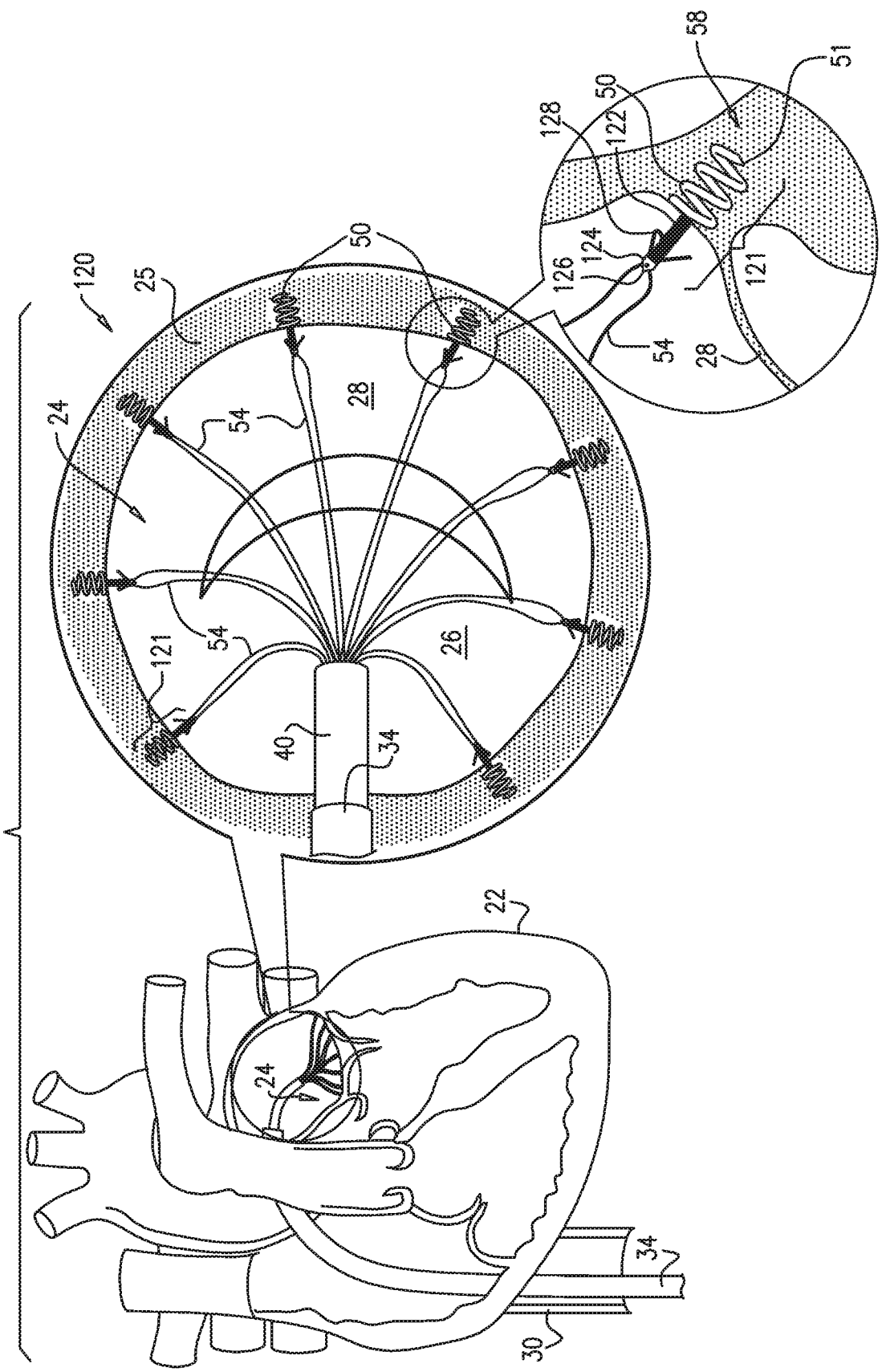
FIGS. 11A-D are schematic illustrations of a transcatheter procedure for implanting a plurality of tissue anchors of FIG. 10, in accordance with some applications of the present invention.

FIG. 11A shows a plurality of tissue anchors 121 implanted along annulus 25, in accordance with some applications of the present invention. Each anchor 121 is reversibly coupled to an elongate delivery tool (not shown for clarity of illustration) and is transcatheterally advanced via the tool toward annulus 25. The delivery tool facilitates corkscrewing of helical tissue anchor 58 into tissue of the annulus. For applications in distal tissue coupling element 50 comprises any other tissue coupling anchor, the delivery tool facilitates coupling of anchor 121 to annulus 25 by advancing distal tissue coupling element 50 into the tissue of annulus 25.

Each anchor 121 is implanted in a manner in which a proximal end of tissue coupling element 50 is disposed within tissue of annulus 25 and a distal end portion of spring 122 is disposed proximally to the surface of annulus 25, as shown in the enlarged image of tissue anchor 121 of FIG. 11A. For some applications of the present invention, delivery tool 42, as described hereinabove with reference to FIGS. 2A-C may be reversibly coupled to each anchor 121 and facilitate implantation of each anchor 121. In such an application, arms 128 of implant-penetrating element 47b are compressed within slit 48 of manipulator 44 of tool 42.

Once tissue anchor 121 is implanted, cord 54 remains coupled to anchor 121, as described hereinabove with reference to the cord 54 coupled to tissue anchor 49. It is to be noted that although eight anchors 121 are implanted around annulus 25 by way of illustration and not limitation, any suitable number of anchors 121 may be implanted along annulus 25 according to the needs of a given patient, e.g., depending on the level of distention and relaxation of the annulus of a given patient.

Figure 11B:
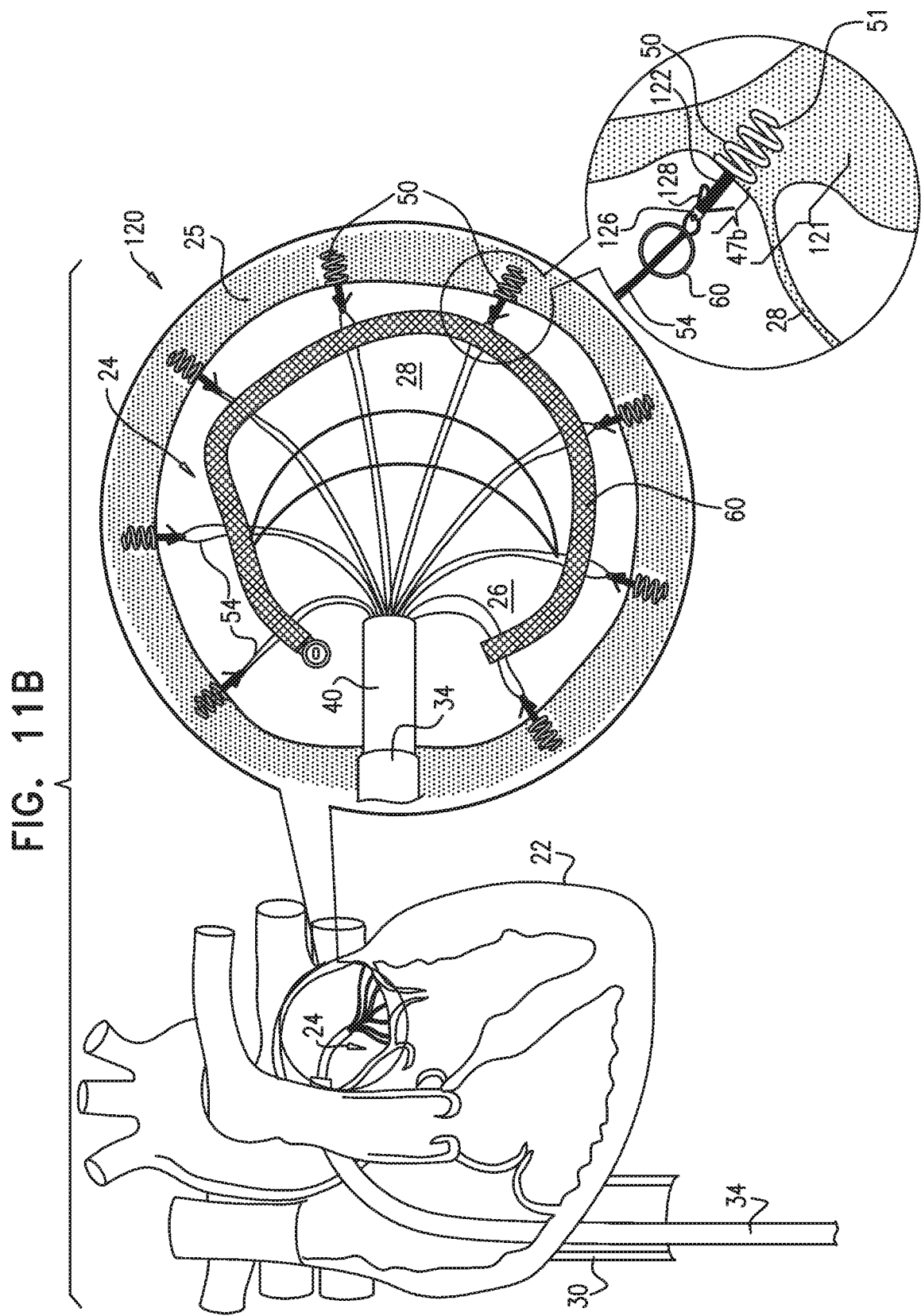

Reference is now made to FIG. 11B, which is a schematic illustration of a tissue-repair implant 60 being advanced along cords 54 toward annulus 25 of the mitral valve of the patient. As shown, repair implant 60 comprises a non-continuous, open, partial annuloplasty ring, by way of illustration and not limitation. It is to be noted that any valve repair implant, e.g., a full annuloplasty ring, a partial annuloplasty ring, or a prosthetic valve, may be advanceable along cords 54. The partial, open ring of repair implant 60 may be implemented using any one of the techniques described in U.S. patent application Ser. No. 12/341,960 to Cabiri, which is incorporated herein by reference.

Implant 60 is advanced along cords 54, in a manner as described hereinabove with reference to FIGS. 2C and 4. A pushing tool (not shown for clarity of illustration) is used to push implant 60 through catheter 40 and toward annulus 25. Implant 60 is pushed until respective portions of a distal surface of implant 60 contact each pointed tip 126 of proximal portion 124 of implant-penetrating element 47b.

Figure 11C:
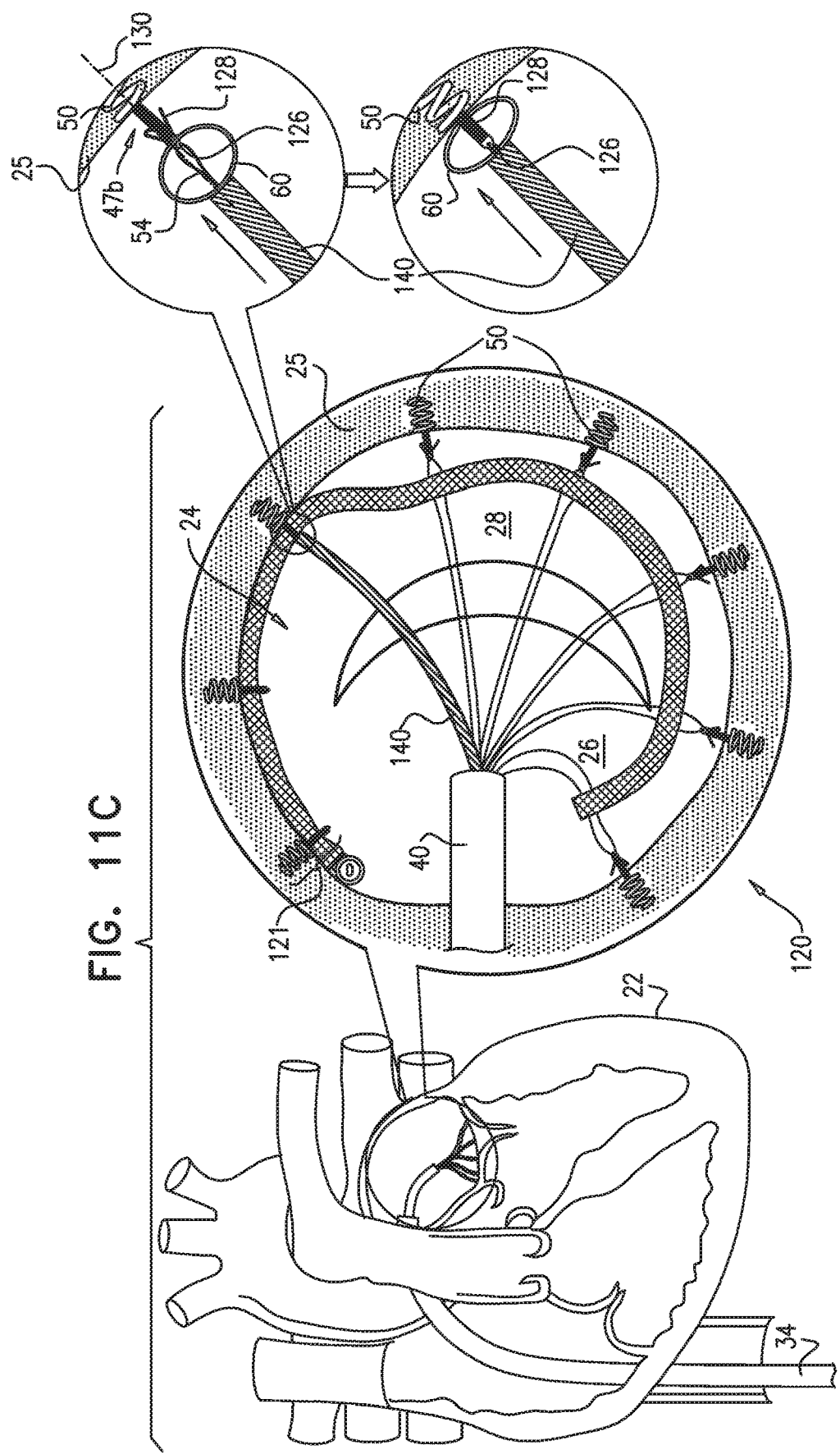

FIG. 11C shows a pushing tool 140, as described hereinabove with reference to FIG. 11B, that pushes respective portions of implant 60 such that they are engaged by each implant-penetrating element 47b of anchors 121, in accordance with some applications of the present invention. Pushing tool 140 is advanced along a respective cord 54, as shown, and toward a portion of implant 60. The physician uses pushing tool 140 to push on the proximal surface of implant 60 such that the distal surface of implant 60 is punctured by pointed tip 126 of implant-penetrating element 47b. Continued pushing of pushing tool 140: (1) advances a portion of implant 60 around arms 128 and along the elastic portion and spring 122 of implant-penetrating element 47b, and thereby (2) facilitates coupling of the portion of implant 60 to anchor 121. As implant 60 is pushed, spring 122 compresses along axis 130 and provides flexibility to system 120, as implant 60 is anchored to annulus 25.

Following the puncturing of the distal surface of the portion of implant 60 by pointed proximal tip 126 of implant-penetrating element 47b, an opening is created at the distal surface of implant 60 for passage therethrough of a proximal portion of implant-penetrating element 47b. As implant 60 is pushed along implant-penetrating element 47b, the proximal portion is disposed within the lumen of implant 60, as shown in the enlarged image of FIG. 11C. The opening at the distal surface of implant 60 that is created by puncturing the material of implant 60 closes around and radially compresses radially-expandable arms 128 as the proximal portion of implant-penetrating element 47b passes through implant 60 in conjunction with the pushing of implant 60 (as shown in the enlarged cross-sectional images of implant 60 being coupled to anchor 121). Radially-expandable arms 128 are compressed such that they align alongside spring 122 as the portion of implant 60 is pushed along implant-penetrating element 47b. Responsively to continued pushing of the portion of implant 60 by tool 140, pointed proximal tip 126 of implant-penetrating element 47b punctures a proximal surface of the portion of implant 60 from within the lumen of implant 60, and proximal tip 126 emerges proximally to the proximal surface of implant 60.

Figure 11D:
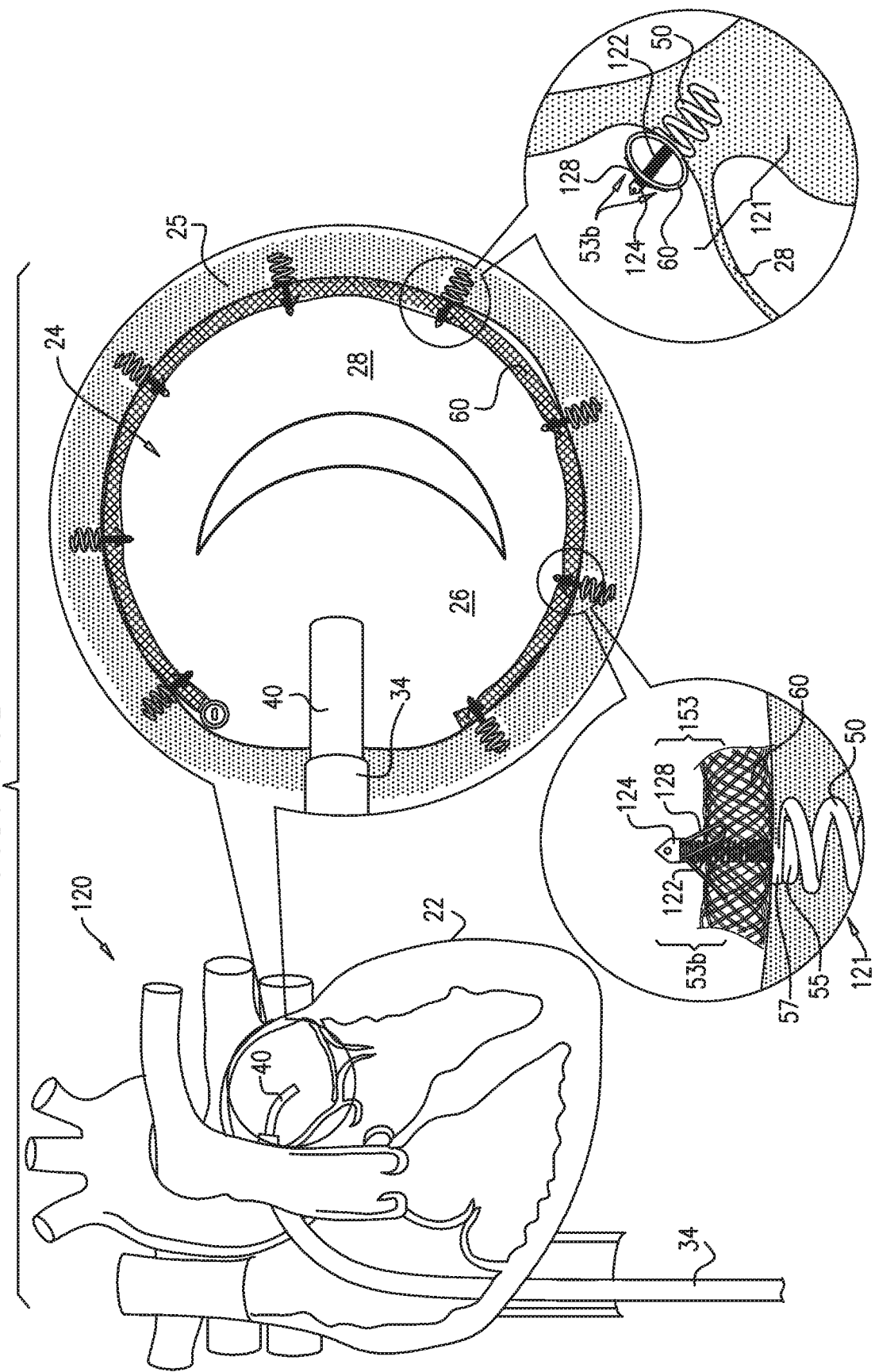

Reference is now made to FIG. 11D, which is a schematic illustration of the locking in place of the portion of implant 60 at a given location along annulus 25 via arms 128 of anchor 121, in accordance with some applications of the present invention. As described hereinabove, responsively to continued pushing of the portion of implant 60 by tool 140, pointed tip 126 of implant-penetrating element 47b punctures and creates an opening at the proximal surface of implant 60 and emerges from within the lumen of implant 60 proximally to the upper surface of implant 60. Responsively to continued pushing of the portion of implant 60 by tool 140, implant 60 slides along implant-penetrating element 47b such that respective distal ends of arms 128 emerge from within the lumen of implant 60 and through the opening at the proximal surface of the portion of implant 60. Once arms 128 are freed from within the lumen of the portion of implant 60 (i.e., are no longer radially compressed by the lumen of the portion of implant 60 and/or the respective openings at the proximal and distal surfaces of the portion of implant 60), arms 128 expand radially, as shown in the enlarged images of FIG. 11D. Arms 128 are configured to radially compress and expand between 0 and 30 degrees with respect to axis 130 of anchor 121. Arms 128 expand such that (1) the proximal ends thereof collectively form a perimeter that is larger than the perimeter of the external surface of implant 60, and (2) arms 128 lock in place around implant 60 to restrict proximal movement of implant 60.

Reference is now made to FIGS. 11C-D. Arms 128 expand around the external surface of implant 60 and thus function as proximal restraining element 53b to restrain proximal sliding of implant 60 along implant-penetrating element 47b and decoupling of implant 60 from anchor 121 (FIG. 11D). Once arms 128 expand and lock in place the portion of implant 60 to annulus 25 via anchor 121, pushing tool 140 is extracted from the body of the patient through catheter 40. Spring 122 is thus no longer compressed responsively to the pushing force of implant 60 applied by tool 140, and spring 122 relaxes and returns to its resting state (FIG. 11D). As shown in FIG. 11C, following the coupling of respective portions of implant 60 to anchors 121, each cord 54 coupled to the respective anchor 121 is cut, as described hereinabove with reference to FIG. 2B, and decoupled from the respective anchor 121. Typically, but not necessarily, each cord 54 is decoupled from anchor 121 immediately following the coupling of the respective portion of implant 60 to each anchor 121 (as shown in FIG. 11C). Alternatively, cords 54 remain coupled to respective anchors 121 until the entire implant 60 is coupled to annulus 25 via anchors 121.

In some embodiments, in conjunction with the pushing of implant 60 by tool 140, cord 54 is pulled taut so as to apply load to spring 122 such that it expands to a length greater than its length during the resting state of spring 122. The pulling of spring 122 helps pull arms 128 through the lumen of implant 60 such that they emerge from within the lumen of implant 60. Once arms 128 emerge from within the lumen of implant 60, cord 54 is no longer pulled, and spring 122 returns to its resting state in order to allow arms 128 to rest against an external proximal surface of implant 60 and restrict proximal movement of implant 60 along implant-penetrating element 47b. Thus, arms 128 function as proximal restraining element 53b, and arms 128 together with portion 124 and tip 126 function as barb 153b.

Reference is again made to FIG. 11C, which shows, by way of illustration and not limitation, implant 60 being coupled to anchors 121 in a systematic order beginning from the left-most anchor 121, (i.e., disposed at 10 o'clock) and moving clockwise in series from anchor to anchor. It is to be noted that implant 60 may be coupled to anchors 121 in any suitable order (i.e., not in series from anchor to anchor), in accordance with the protocol of the operating physician.

Reference is now made to FIGS. 12-14, which are schematic illustrations of a system 200 for implanting anchors 49 and 121 described hereinabove in an open-heart or minimally-invasive procedure, in accordance with some applications of the present invention. System 200 comprises a tool body 202 and proximal handle portions 204 and 206. Tool body 202 comprises an outer tube shaft 210 and an inner tube shaft 212 (FIG. 14). Inner tube shaft 212 functions similarly to the elongate tube shaft of delivery tool 42, as described hereinabove with reference to FIGS. 2A-C. The distal end of tube shaft 212 is coupled to manipulator 44 that is described hereinabove with reference to FIGS. 2A-C. Manipulator 44 is reversibly coupled to anchor 49, as described hereinabove. It is to be noted that although FIGS. 12-14 show manipulator 44 coupled to anchor 49, manipulator 44 may also be coupled to anchor 121, in a manner as described hereinabove with reference to FIG. 11A. The proximal end of inner tube shaft 212 is coupled to handle portion 206 of tool body 202. For some applications, handle portion 206 is rotatable along an axis 230 of tool body 202 in order to (1) rotate inner tube shaft 212 and, thereby, rotate manipulator 44, and thereby (2) facilitate corkscrewing of distal tissue coupling element 50 of anchor 49 into tissue of annulus 25. Alternatively, the entire tool body 202 is rotated about axis 230 of tool body 202 in order to rotate distal tissue coupling element 50 of anchor 49 and facilitate corkscrewing of distal tissue coupling element 50 of anchor 49 into tissue of annulus 25. In either application, following the corkscrewing of distal tissue coupling element 50 into tissue of annulus 25, anchor 49 is decoupled from manipulator 44, as described hereinabove with reference to FIG. 2B, and thereby decoupled from tool body 202.

As shown in FIG. 14, inner tube shaft 212 is housed within a lumen of outer tube shaft 210. Inner tube shaft 212 and handle portions 204 and 206 are each shaped to provide a lumen for passage therethrough of cord 54 coupled to anchor 49. Tool body 202 is shaped so as to provide (1) a proximal opening 214 for passage therethrough of cord 54, and (2) a distal opening 216 for passage therethrough of anchor 49. Once distal tissue coupling element 50 of anchor 49 is corkscrewed into tissue of annulus 25 and anchor 49 is decoupled from manipulator 44, tool body 202 is slid proximally along cord 54 leaving anchor 49 and a portion of cord 54 in heart 22 of the patient.

Figure 15:
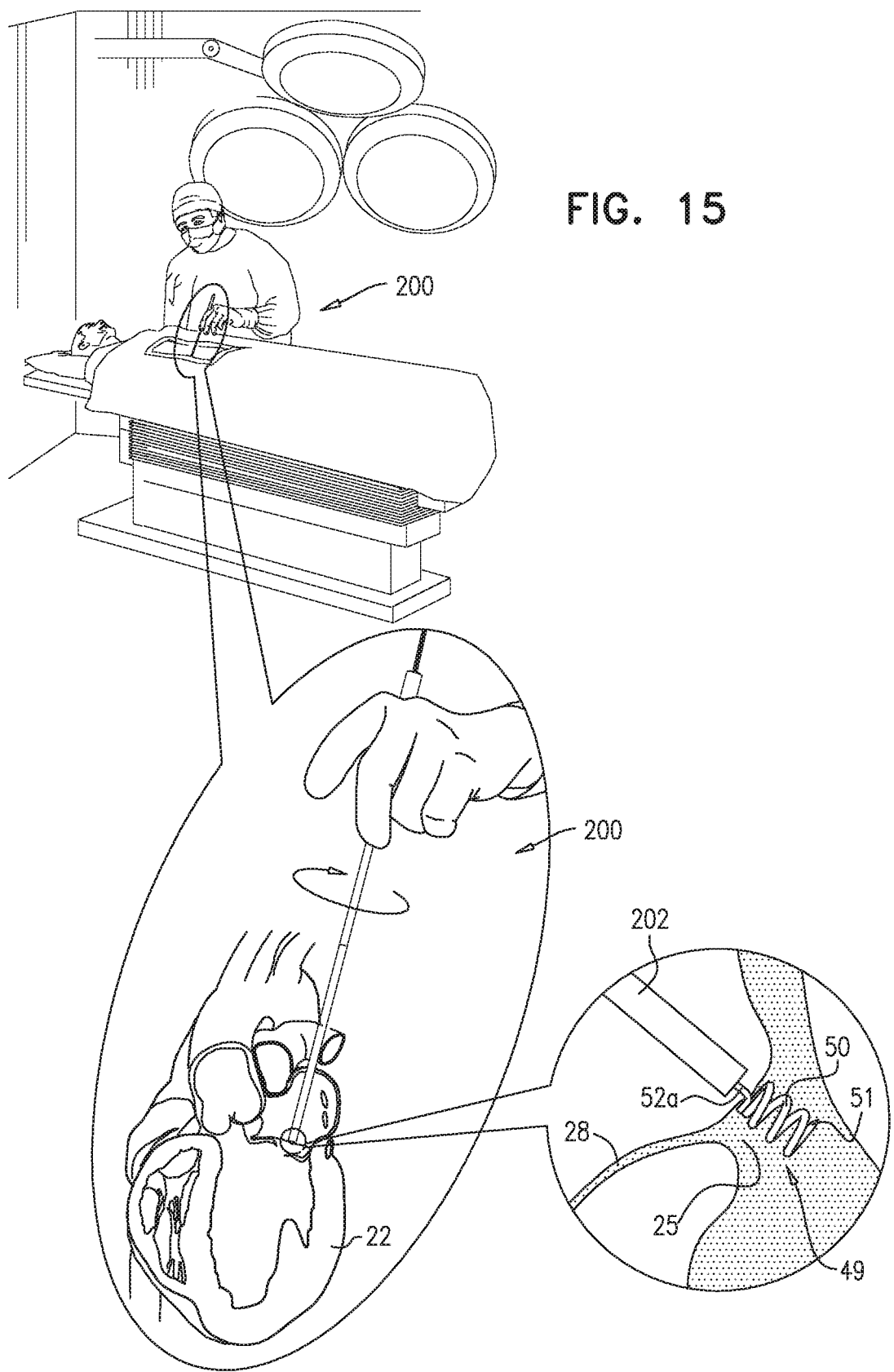
FIGS. 15-18 are schematic illustrations of the implantation and locking of the valve-repair implant during the minimally-invasive or open-heart procedure, in accordance with some applications of the present invention.

FIG. 15 shows system 200 being used to implant anchor 49 in heart 22 of the patient, in accordance with some applications of the present invention during an open-heart or minimally-invasive procedure. In these procedures, an incision is created in heart 22 at the left atrium to provide a passage for the distal end portion of tool body 202 to access an atrial surface of the mitral valve. As shown, tool body 202 (or tube shaft 212) is rotated in order to facilitate corkscrewing of distal tissue coupling element 50 of anchor 49 into tissue of annulus 25. As described hereinabove, pointed distal tip 51 punctures tissue of annulus 25 in order to facilitate corkscrewing of distal tissue coupling element 50 into tissue of annulus 25.

Figure 16:
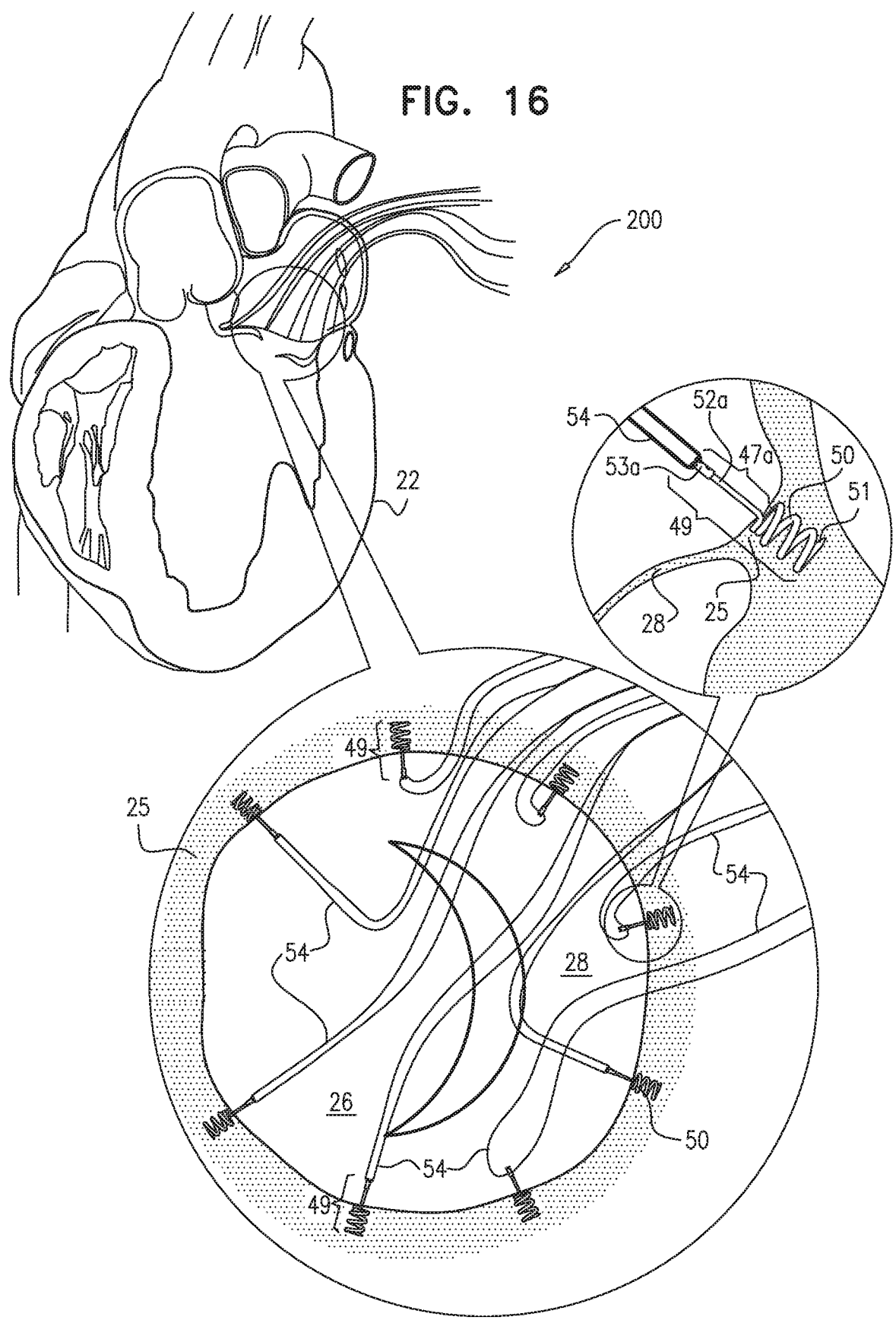

FIG. 16 shows a plurality of anchors 49 implanted along annulus 25 following the corkscrewing of distal tissue coupling element 50 of each anchor 49 into tissue of annulus 25, as facilitated by tool body 202 of system 200 described hereinabove with reference to FIGS. 12-14, in accordance with some applications of the present invention. It is to be noted that anchors 121, as described hereinabove with reference to FIGS. 10 and 11A-D, may be implanted along annulus 25 using tool body 202 of system 200. Following the implantation of each anchor 49 via tool body 202, respective cords 54 remain coupled to each anchor 49. The proximal end portions of each cord 54 are accessible outside the body of the patient.

As shown, each distal tissue coupling element 50 is disposed within tissue of annulus 25, and each proximal restraining element 53a and post 52a of each anchor 49 extend proximally from the proximal surface of annulus 25. Each implant-penetrating element 47a comprising proximal restraining element 53a and post 52a is thus accessible by any tissue-repair implant 60 advanced theretoward along cord 54 reversibly coupled to proximal restraining element 53a.

Figure 17:
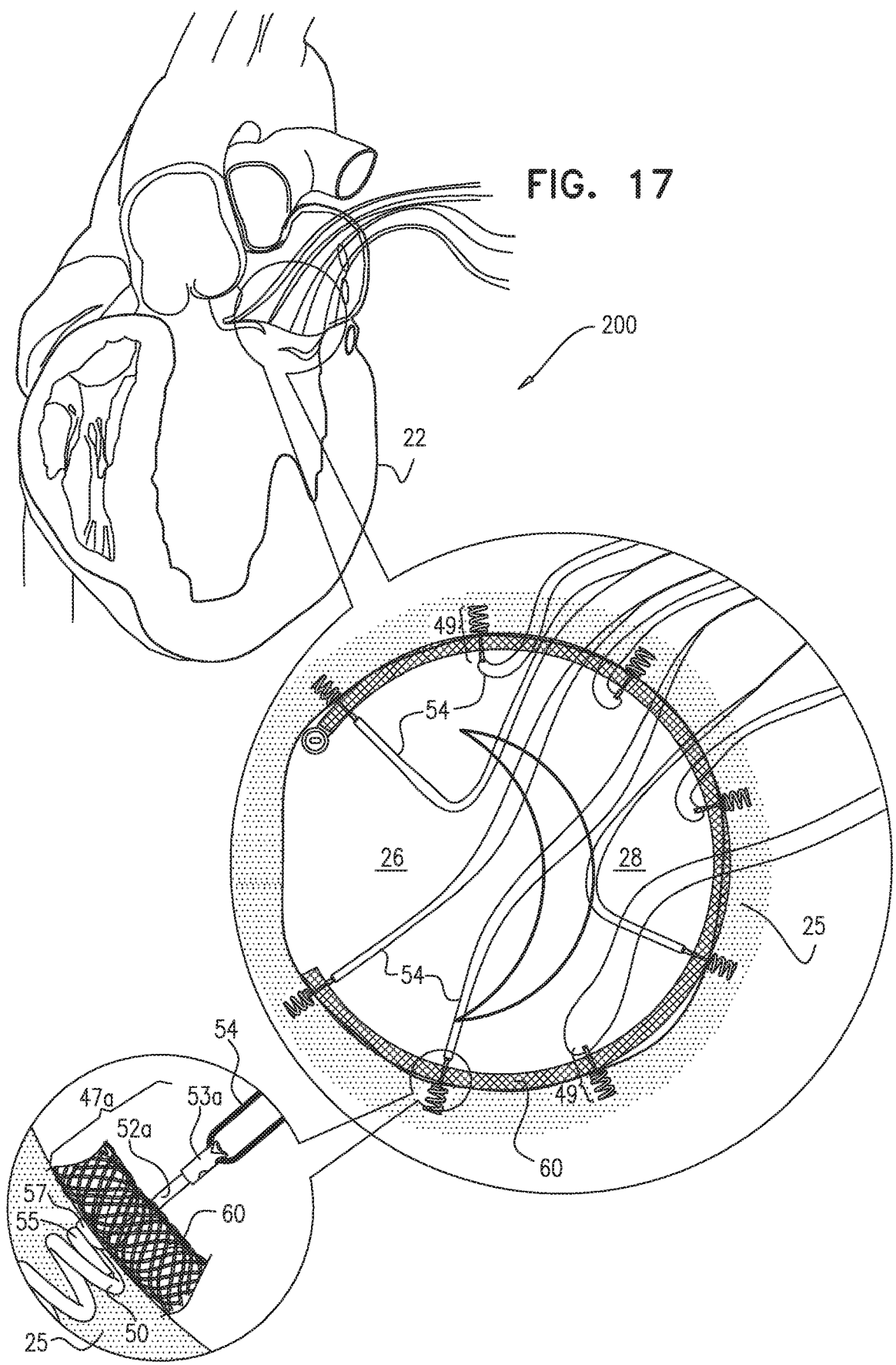

FIG. 17 shows tissue-repair implant 60, as described hereinabove, coupled to annulus 25 via anchor 49, in accordance with some applications of the present invention. As described hereinabove, implant 60 is advanced along cords 54 toward tissue of annulus 25. A tool may be used to advance respective portions of implant 60 along each cord 54. Alternatively, during an open-heart procedure, the physician uses his or her fingers to push respective portions of implant 60 along each cord 54. As shown in the enlarged image of FIG. 17, a portion of implant 60 is coupled to anchor 49 in a manner in which: (1) the distal surface of the portion of implant 60 contacts the proximal surface of annulus 25, (2) a distal portion of post 52a is disposed within the lumen of implant 60, and (3) a distal end of proximal restraining element 53a is disposed proximally to a proximal surface of the portion of implant 60. As shown, cords 54 remain coupled to anchors 49 following the coupling of the respective portions of implant 60 to implant-penetrating element 47a of each anchor 49.

Figure 18:
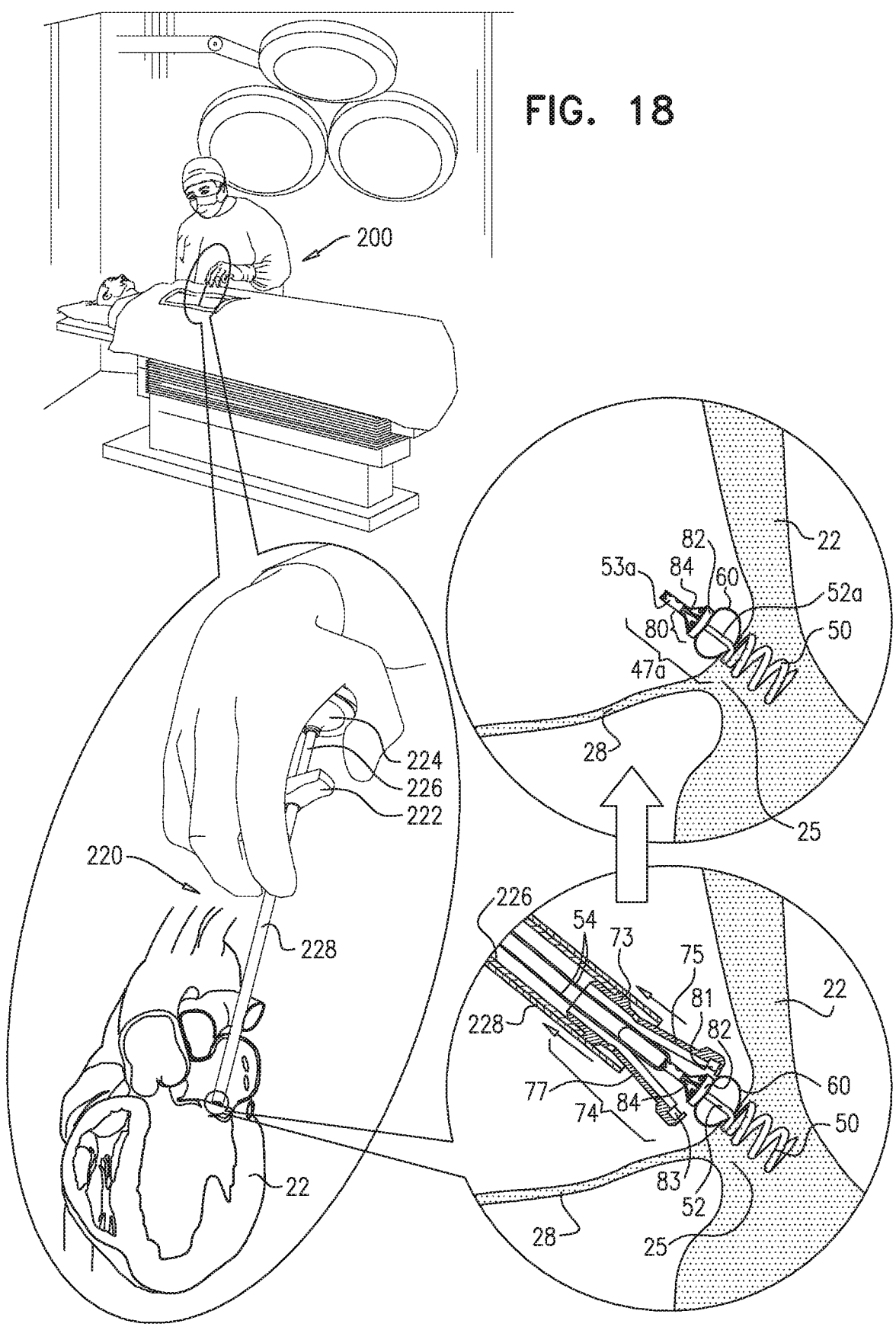

FIG. 18 shows a tool system 220 for coupling a respective lock 80 to a portion of implant-penetrating element 47a that is distal to proximal restraining element 53a of each anchor 49, in accordance with some applications of the present invention. Tool system 220 comprises an outer tube shaft 228 which is shaped to provide a lumen for slidable movement of an inner tube shaft 226. As shown in the enlarged cross-sectional image of FIG. 18, tube shaft 226 is shaped so as to provide a lumen for passage therethrough of cord 54 in order to facilitate sliding of tool system 220 along cord 54 and toward anchor 49.

A distal end of inner tube shaft 226 is coupled to locking mechanism 74 comprising lock holder 73, as described hereinabove with reference to FIGS. 5A-B. Thus, inner tube shaft 226 functions similarly to advancement tube 72 (as described hereinabove with reference to FIGS. 5A-B) in order to advance locking mechanism distally through outer tube shaft 228. Outer tube shaft 228 functions similarly to overtube 70 (as described hereinabove with reference to FIGS. 5A-B) in order to surround radially-expandable arms 75 and 77 of locking mechanism 74 and maintain arms 75 and 77 in a compressed state within a distal portion of shaft 228 during a resting state of system 220. As described hereinabove, lock holder 73 of locking mechanism 74 is reversibly coupled to a lock 80 which locks in place a portion of implant 60 to annulus 25 via anchor 49.

A proximal portion of inner tube shaft 226 is coupled to a first engageable element 222, while a proximal end of outer tube shaft 228 is coupled to a second engageable element 224. First and second engageable elements 222 and 224 are engageable by the hand of the operating physician. Tool system 220 is spring-loaded so as to facilitate controlled displacement of second engageable element 224 from first engageable element 222. Responsively to pulling of second engageable portion element 224 away from first engageable element 222, outer tube shaft 228 slides proximally along inner tube shaft 226.

Prior to the pulling of second engageable element 224, the operating physician pushes the entire tool system 220 (i.e., without pulling second engageable element 224 away from first engageable element 222) such that (1) the distal end of outer tube shaft 228 contacts the proximal surface of implant 60, and (2) lock 80 is pushed along proximal restraining element 53a and engages post 52a, in a manner as described hereinabove with reference to FIGS. 5A-B, 6A-B, and 7. The physician then pulls second engageable element 224 away from first engageable element 222. In response to the pulling of engageable element 224 (i.e., a pulled state of system 220), tube shaft 228 is pulled and a distal portion of lock holder 73 is exposed distally to the distal end of outer tube shaft 228. Arms 75 and 77 are freed from within a distal end portion of outer tube shaft 228 and radially expand. Annular distal portion 82 of lock 80 is then freed from within slots 81 and 83 of arms 75 and 77, respectively, and lock 80 is decoupled from locking mechanism 74 and tool system 220. Once lock 80 is locked in place between implant 60 and proximal restraining element 53a, cord 54 is clipped distally to proximal end portion 59 thereof so as to create free ends of cord 54, and cord 54 is extracted from within the body of the patient, as described hereinabove with reference to FIGS. 2C and 7.

As shown in the enlarged cross-sectional images of FIG. 18, a distal portion of post 52a couples implant 60 to anchor 49 by being disposed within the lumen of implant 60 between a first opening of implant 60 at a distal surface thereof and a second opening of implant 60 at a proximal surface thereof.

Reference is now made to FIG. 19, which is a schematic illustration of a system 320 comprising a tissue anchor 321 that is similar to tissue anchor 49, as described hereinabove, with the exception that distal tissue coupling element 50 comprises an expandable tissue anchor 322 which comprises one or more, e.g., a plurality of, radially-expandable prongs 326, in accordance with some applications of the present invention. Prongs 326 comprise flexible metal, e.g., nitinol or stainless steel, and have a tendency to expand radially, as shown in the left-most image in FIG. 19. Anchors 322 facilitate coupling of tissue anchor 321 to annulus 25 of the native valve, such as the mitral valve or the tricuspid valve, or to any other valve or tissue. Tissue anchor 322 is shaped so as to define a pointed distal tip 324 configured to puncture tissue of annulus 25. As described hereinabove, distal tissue coupling element 50, which, for this application of the present invention comprises tissue anchor 322, has length L3 of 2-8 mm, e.g., 4 mm.

Tissue anchor 322 is coupled to (e.g., welded or otherwise coupled to) post 52a of implant-penetrating element 47a, as described hereinabove. Implant-penetrating element 47a has length L2 of 4-10 mm, e.g., 5.5 mm. Taken together, tissue anchor 321 has length L1 of 6-18 mm, e.g., 10 mm.

In the right-side images of FIG. 19, tissue anchor 322 is shown being implanted into tissue of annulus 25. Pointed distal tip 324 punctures tissue of annulus 25. In response to distal pushing of anchor 321, tissue anchor 322 is pushed within tissue of annulus 25. As anchor 321 is pushed, the force of the tissue of annulus 25 pushes against prongs 326 and compresses prongs 326 inwardly (as shown in the upper-right image). Following the pushing of anchor 321 distally, anchor 321 is pulled slightly proximally (e.g., by pulling on cord 54) in order to enable prongs 326 to expand radially to assume a flower shape and a larger surface area, to restrict proximal motion of anchor 321 in tissue of annulus 25.

Following the implanting of anchor 322 within tissue of annulus 25, post 52a remains disposed proximally to a surface of annulus 25, so that it can puncture and receive the implant, as described hereinabove.

FIG. 20 shows a system 420 comprising a tissue anchor 421 that is similar to tissue anchor 121, as described hereinabove, with the exception that distal tissue coupling element 50 comprises an expandable tissue anchor 322, as described hereinabove with reference to FIG. 19, in accordance with some applications of the present invention. As described hereinabove, distal tissue coupling element 50, which, for this application of the present invention comprises tissue anchor 322, has length L3 of 2-8 mm, e.g., 4 mm. Also, as described hereinabove, anchor 421 comprises a proximal elastic portion which comprises tension spring 122, as shown by way of illustration and not limitation. Implant-penetrating element 47b has a length L4 of between 3 mm and 5 mm, e.g., 4 mm, when spring 122 is relaxed. Thus, for some applications, anchor 421 has a total length L5 of 5-13 mm.

Tissue anchor 421 comprises distal tissue coupling element 50 and proximal implant-penetrating element 47b. As described hereinabove, implant-penetrating element 47b comprises the proximal elastic portion comprising tension spring 122 and proximal restraining element 53b comprising radially-expandable anchor arms 128. Implant-penetrating element 47b comprises a proximal portion 124 shaped to define a pointed tip 126 for penetrating an implant (e.g., a tissue-repair implant 60) and facilitating passage of the implant over implant-penetrating element 47b. Typically, proximal portion 124, pointed tip 126, and arms 128 together form and function as a barb 153.

Reference is now made to FIGS. 19 and 20. For some applications of the present invention, during the delivery of anchors 321 and 421 toward annulus 25, a sheath (not shown) surrounds prongs 326 so as to keep them in a closed state and facilitate atraumatic advancement of prongs 326 toward tissue at annulus 25.

Reference is now made to FIGS. 1A-F, 2A-C, 3-4, 5A-B, 6A-B, 7-10, 11A-D, and 12-20. It is to be noted that systems, methods, and anchors 49, 121, 321, and 421 described herein may be used at any atrioventricular valve, e.g., the mitral valve or the tricuspid valve. It is to be further noted that systems, methods, and anchors 49, 121, 321, and 421 described herein may be implanted at any suitable tissue site (e.g., tissue of a stomach of the patient) in order to facilitate implantation of any suitable implant.

For some applications of the present invention, techniques described herein are practiced in combination with techniques described in one or more of the references cited in the Background section of the present patent application.

Additionally, the scope of the present invention includes applications described in one or more of the following:

PCT Publication WO 06/097931 to Gross et al., entitled, "Mitral Valve treatment techniques," filed Mar. 15, 2006;

U.S. Provisional Patent Application 60/873,075 to Gross et al., entitled, "Mitral valve closure techniques," filed Dec. 5, 2006;

U.S. Provisional Patent Application 60/902,146 to Gross et al., entitled, "Mitral valve closure techniques," filed Feb. 16, 2007;

U.S. Provisional Patent Application 61/001,013 to Gross et al., entitled, "Segmented ring placement," filed Oct. 29, 2007;

PCT Publication WO 08/068756 to Gross et al., entitled, "Segmented ring placement," filed Dec. 5, 2007;

U.S. patent application Ser. No. 11/950,930 to Gross et al., entitled, "Segmented ring placement," filed Dec. 5, 2007, which published as US 2008/0262609 and which issued as U.S. Pat. No. 8,926,695;

U.S. patent application Ser. No. 12/435,291 to Maisano et al., entitled, "Adjustable repair chords and spool mechanism therefor," filed on May 4, 2009, which published as US 2010/0161041, and which issued as U.S. Pat. No. 8,147,542;

U.S. patent application Ser. No. 12/437,103 to Zipory et al., entitled, "Annuloplasty ring with intra-ring anchoring," filed on May 7, 2009 which issued as U.S. Pat. No. 8,715,342;

PCT Publication WO 10/004546 to Gross et al., entitled, "Annuloplasty devices and methods of delivery therefor," filed on Jun. 15, 2009;

U.S. patent application Ser. No. 12/548,991 to Maisano et al., entitled, "Implantation of repair chords in the heart," filed on Sep. 21, 2009, which published as US 2010/0161042, and which issued as U.S. Pat. No. 8,808,368;

PCT Publication WO 10/073246 to Cabiri et al., entitled, "Adjustable annuloplasty devices and mechanisms therefor," filed Dec. 22, 2009;

U.S. patent application Ser. No. 12/706,868 to Miller et al., entitled, "Actively-engageable movement-restriction mechanism for use with an annuloplasty structure," filed Feb. 17, 2010, which published as US 2010/0211166, and which issued as U.S. Pat. No. 8,353,956;

PCT Patent Application PCT/IL2010/000357 to Maisano et al., entitled, "Implantation of repair chords in the heart," filed May 4, 2010, which published as WO 10/128502; and/or PCT Patent Application PCT/IL2010/000358 to Zipory et al., entitled, "Deployment techniques for annuloplasty ring and over-wire rotation tool," filed May 4, 2010, which published as WO 10/128503.

All of these applications are incorporated herein by reference. Techniques described herein can be practiced in combination with techniques described in one or more of these applications.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A tissue anchor for use with a valve-repair implant configured to be coupled to cardiac tissue of a patient, the tissue anchor comprising:
   a distal tissue coupling element configured to couple the tissue anchor to the cardiac tissue by penetrating distally into the cardiac tissue; and
   a proximal implant-penetrating element configured to penetrate proximally into at least a portion of the valve-repair implant and facilitate coupling of the valve-repair implant to the tissue anchor, the proximal implant-penetrating element comprising:
      a protrusion protruding proximally from the distal tissue coupling element into a plane of the implant and to couple the implant to the tissue anchor; and
      an implant-restraining element coupled to the protrusion, and configured to restrain the valve-repair implant from separating from the implant-penetrating element.

2. The tissue anchor according to claim 1, wherein the implant-restraining element is shaped so as to define a distal shelf that has a transverse cross-sectional length that is larger than a transverse cross-sectional length of the protrusion, the distal shelf being configured to facilitate restricting of proximal motion of the implant along the protrusion.

3. The tissue anchor according to claim 1, further comprising a cord removably couplable to the tissue anchor, the cord being configured to facilitate passage of the implant therealong and toward the tissue anchor.

4. The tissue anchor according to claim 3, wherein the protrusion comprises a post.

5. The tissue anchor according to claim 4, wherein the post has a length of between 1 and 7 mm and a greatest cross-sectional area of between 0.03 mm^2 and 0.2 mm^2, which length is at least 4 times the square root of the greatest cross-sectional area.

6. The tissue anchor according to claim 4, wherein the implant-restraining element has a greatest cross-sectional area that is at least 1.5 times a greatest cross-sectional area of the post.

7. The tissue anchor according to claim 6, further comprising a lock configured to be advanced toward the anchor and disposed between the implant and the implant-restraining element, the lock comprising:
   a distal portion configured to rest against the implant; and
   an expandable proximal portion having a cross-sectional area during a resting state of the lock that is larger than the greatest cross-sectional area of the post and smaller than the greatest cross-sectional area of the implant-restraining element.

8. The tissue anchor according to claim 1, wherein the implant-restraining element comprises a barb configured to restrict proximal movement of the implant along the implant-penetrating element.

9. The tissue anchor according to claim 8, wherein the barb comprises one or more arms that are radially expandable to rest against an external surface of the implant following coupling of the implant to the implant-penetrating element.

10. The tissue anchor according to claim 9, wherein the arms are radially collapsible during at least a portion of the coupling of the implant to the implant-penetrating element.

11. The tissue anchor according to claim 8, wherein the proximal implant-penetrating element comprises an elastic portion that is configured to assume a first length when relaxed, and a second, greater length when under load.

12. The tissue anchor according to claim 1, wherein the distal tissue coupling element and the proximal implant-penetrating element are fabricated from a single piece.

13. The tissue anchor according to claim 1, wherein the implant-restraining element is configured to pass proximally through the portion of the implant.

14. The tissue anchor according to claim 1, where the tissue anchor is for use with a valve-repair implant selected from the group consisting of: a full annuloplasty ring, a partial annuloplasty ring, a prosthetic valve, and a docking station for a prosthetic valve.

15. A tissue anchor for use with a valve-repair implant configured to be coupled to cardiac tissue of a patient, the tissue anchor comprising:
   a distal tissue coupling element configured to couple the tissue anchor to the cardiac tissue of the patient; and
   a proximal implant-penetrating element configured to penetrate at least a portion of the valve-repair implant and facilitate coupling of the valve-repair implant to the tissue anchor, the proximal implant-penetrating element comprising:
      a post; and
      an implant-restraining element coupled to a portion of the post, the implant-restraining element being configured to restrain the valve-repair implant from separating from the implant-penetrating element, wherein the implant-restraining element has a greatest cross-sectional area that is at least 1.5 times a greatest cross-sectional area of the post.

16. The tissue anchor according to claim 15, further comprising a cord couplable to the tissue anchor, the cord being configured to facilitate passage of the implant therealong.

17. The tissue anchor according to claim 15, further comprising a lock configured to be advanced toward the anchor, the lock comprising a distal portion configured to rest against the implant.

18. A tissue anchor for use with a valve-repair implant configured to be coupled to cardiac tissue of a patient, the tissue anchor comprising:
   a distal tissue coupling element configured to couple the tissue anchor to the cardiac tissue of the patient; and
   a proximal implant-penetrating element configured to penetrate at least a portion of the valve-repair implant and facilitate coupling of the valve-repair implant to the tissue anchor, the proximal implant-penetrating element comprising:
an implant-restraining element configured to restrain the valve-repair implant from separating from the implant-penetrating element, wherein the implant-restraining element comprises a barb, the barb:
  comprising one or more arms that are radially expandable to rest against an external surface of the implant following coupling of the implant to the implant-penetrating element, and
  configured to restrict proximal movement of the implant along the implant-penetrating element.

* * * * *